(12) United States Patent
Hamazaki

(10) Patent No.: US 8,333,693 B2
(45) Date of Patent: Dec. 18, 2012

(54) ENDOSCOPE PLUG BODY BREAKABLE IN TWO STAGES

(75) Inventor: Masanori Hamazaki, Hachioji (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 1399 days.

(21) Appl. No.: 11/670,782

(22) Filed: Feb. 2, 2007

(65) Prior Publication Data

US 2007/0184717 A1 Aug. 9, 2007

Related U.S. Application Data

(63) Continuation of application No. PCT/JP2005/013967, filed on Jul. 29, 2005.

(30) Foreign Application Priority Data

Aug. 4, 2004 (JP) .................................. 2004-228442
Jun. 16, 2005 (JP) .................................. 2005-176667

(51) Int. Cl.
*A61B 1/00* (2006.01)
*A61B 1/12* (2006.01)
*A61M 5/00* (2006.01)

(52) U.S. Cl. ......... 600/154; 600/153; 600/159; 604/110

(58) Field of Classification Search .......... 600/121–123, 600/153–159; 604/110, 111, 256; 215/250–257
See application file for complete search history.

(56) References Cited

U.S. PATENT DOCUMENTS 5,104,379 A * 4/1992 Nakamura et al. ............. 604/111
5,147,305 A * 9/1992 Nakamura et al. ............. 604/110

FOREIGN PATENT DOCUMENTS

| JP | 03-047275 | 2/1991 |
| JP | 03-073168 | 3/1991 |
| JP | 4-329921 | 11/1992 |

OTHER PUBLICATIONS

International Search Report dated Oct. 4, 2005 in connection with corresponding application No. PCT/JP2005/013967.

* cited by examiner

*Primary Examiner* — Matthew J Kasztejna
*Assistant Examiner* — Ryan Henderson
(74) *Attorney, Agent, or Firm* — Ostrolenk Faber LLP

(57) ABSTRACT

An endoscope plug body includes a plug frame with which a venting cap is covered, an inner peripheral surface being formed in the venting cap, the inner peripheral surface being communicated with a channel arranged in an endoscope. The plug frame includes a latch member that latches the plug frame along the periphery of the venting cap to attach the plug frame to the venting cap; and a breaking member that breaks a partial area of the plug frame while maintained in a continuous state in a circumferential direction of the plug frame, the partial area reaching one end portion of the plug frame while including a part of a latched portion of the latch member.

11 Claims, 19 Drawing Sheets

ENDOSCOPE PLUG BODY BREAKABLE IN TWO STAGES

CROSS-REFERENCE TO RELATED APPLICATIONS

This application is a continuation of PCT international application Ser. No. PCT/JP2005/013967 filed Jul. 29, 2005 which designates the United States, incorporated herein by reference, and which claims the benefit of priority from Japanese Patent Applications No. 2004-228442, filed Aug. 4, 2004 and No. 2005-176667, filed Jun. 16, 2005, incorporated herein by reference.

BACKGROUND OF THE INVENTION

1. Field of the Invention

The present invention relates to an endoscope plug body, particularly to the endoscope plug body which is attached to a channel opening of a treatment instrument insertion channel provided in an endoscope and shields the inside of the treatment instrument insertion channel from the outside in an airtight manner even if a treatment instrument is inserted from the channel opening into the treatment instrument insertion channel.

2. Description of the Related Art

Conventionally, the endoscope is widely used in a medical field and the like. Various treatments are performed to a region, a tissue, and the like in a body cavity of a patient using the endoscope. Specifically a treatment in which a catheter is inserted into the treatment instrument insertion channel provided in the endoscope to inject chemicals into the body cavity of the patient, a treatment in which a forceps is inserted into the treatment instrument insertion channel to ablate or sample a lesional region, and the like are performed.

In performing the treatment with the endoscope, the treatment instrument such as the catheter and the forceps is introduced into the treatment instrument insertion channel through a plug body which is attached to the channel opening provided in an operation portion of the endoscope. The plug body prevents a body fluid, filth, air, and the like from flowing back through the treatment instrument insertion channel to leak out to the outside from the channel opening because of a change in internal pressure of the body cavity.

The plug body includes a reuse type plug body and a disposable type plug body. The reuse type plug body can be reused by cleaning and disinfecting the plug body after each use. The disposable type plug body cannot be reused by forming the plug body with necessary breakage in detaching the plug body, when the plug body is once mounted in the opening of the treatment instrument insertion channel.

Examples of the disposable type plug body include plug bodies proposed in Japanese Patent Application Laid-Open (JP-A) No. H3-073168 and JP-A No. H3-047275. JP-A No. H3-073168 discloses a medical instrument plug body having a configuration, in which an annular cut groove is formed in an outer peripheral surface of a plug frame, a thickness is reduced in the cut groove, and a knob is provided in the outer peripheral surface below the cut groove while being integral with the plug frame. In the configuration disclosed in JP-A No. H3-073168, when the knob is pulled toward a circumferential direction after use by grabbing the knob with the fingers, the plug frame is sequentially broken from the cut groove toward the annular cut groove, and the plug frame is divided into two upper and lower portions from the cut groove to extremely easily detach the plug body from the insertion port body such as the channel opening.

There is also disclosed a medical instrument plug body having a configuration in which the knob is formed in a lower end of a cylindrical side wall of the plug frame while being integral with the plug body, and two cuts are continuously formed upward in an outer surface portion of the plug frame from both ends of a connection portion where the knob is connected to the plug frame so as to reach at least a portion above the annular groove portion. In the configuration, the knob is pulled after use by grabbing the knob with the fingers. Then, the cut groove is vertically broken upward, and a part of the annular groove portion is lacked in an arc to easily detach the plug body from the insertion port body.

On the other hand, JP-A No. H3-047275 discloses a medical instrument plug body having a configuration, in which the knob is provided in the lower end of the cylindrical side wall of the plug body while being integral with the main body portion, cut portions are formed at both ends of the knob with respect to the main body portion, and groove portions connected to the cut portions respectively are continuously provided so as to reach the side above the annular groove portion. In the configuration, when the knob is pulled by grabbing the knob with the fingers, a part of the annular groove portion is lacked while the plug body is broken from the cut portion to the groove portion, so that the plug body is easily detached from the insertion port body.

There is also disclosed a medical instrument plug body having a configuration in which one cut portion is provided on one side of the connection portion between the knob and the main body portion, and one groove portion connected to the cut portion is formed in a spiral shape in a side wall portion of the main body portion while continued to the upper portion of the annular groove portion. In the configuration, when the knob is pulled, the plug body is broken in the spiral shape from the cut portion to the groove portion, and a part of the annular groove portion fitted in a flange portion is largely broken to easily detach the plug body from the insertion port body.

There is also disclosed another medical instrument plug body having a configuration in which a notch portion to be caught by the finger is provided in an upper side face of the main body of the plug body, a pair of groove portions is provided along an outer periphery of the main body portion while continued to the notch portion, and a breaking band portion is formed as a thin portion between the pair of groove portions. In this case, the pair of groove portions is not provided in the whole circumference of the main body portion, but the pair of groove portions is formed downward at the position on the substantially symmetrical side opposite to the notch portion so as to reach the lower end of the main body portion. In the configuration, the finger is inserted into the notch portion to pick the plug body upward, and thereby the upper portion of the main body portion is broken. Then, after the plug body is pulled hard upward, the plug body is pulled toward the front side (downward), and thereby the breaking band portion is continuously broken and detached from the insertion port.

There is also disclosed still another medical instrument plug body having a configuration in which the knob is provided at an edge portion in the upper end of the cylindrical side wall of the plug body while integral with the main body portion of the plug body, the cut portion is formed along a half circumference of the cylindrical side wall of the plug body, and the cut portion is provided above the annular groove portion. In the configuration, when the knob is pulled upward by grabbing the knob with the fingers, the plug body is broken from the weakest cut portion, and the annular groove portion fitted in the flange portion can be disengaged to detach the plug body from the insertion port body.

SUMMARY OF THE INVENTION

An endoscope plug body according to an aspect of the present invention includes a plug frame with which a venting cap is covered, an inner peripheral surface being formed in the venting cap, the inner peripheral surface being communicated with a channel arranged in an endoscope. The plug frame includes a latch member that latches the plug frame along the periphery of the venting cap to attach the plug frame to the venting cap; and a breaking member that breaks a partial area of the plug frame while maintained in a continuous state in a circumferential direction of the plug frame, the partial area reaching one end portion of the plug frame while including a part of a latched portion of the latch member.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 8 is a sectional view taken along line A-A of FIG. 4;

FIG. 29 is an appearance view showing a state in which the endoscope plug body is detached from the channel opening when viewed from a side face of the endoscope plug body;

FIG. 34 is an appearance view showing a state in which the endoscope plug body is detached from the channel opening when viewed from the side face of the endoscope plug body;

DETAILED DESCRIPTION OF THE PREFERRED EMBODIMENTS

Exemplary embodiments of the endoscope plug body of the invention will be described below with reference to the drawings. However, the invention is not limited to the embodiments.

Figure 1:
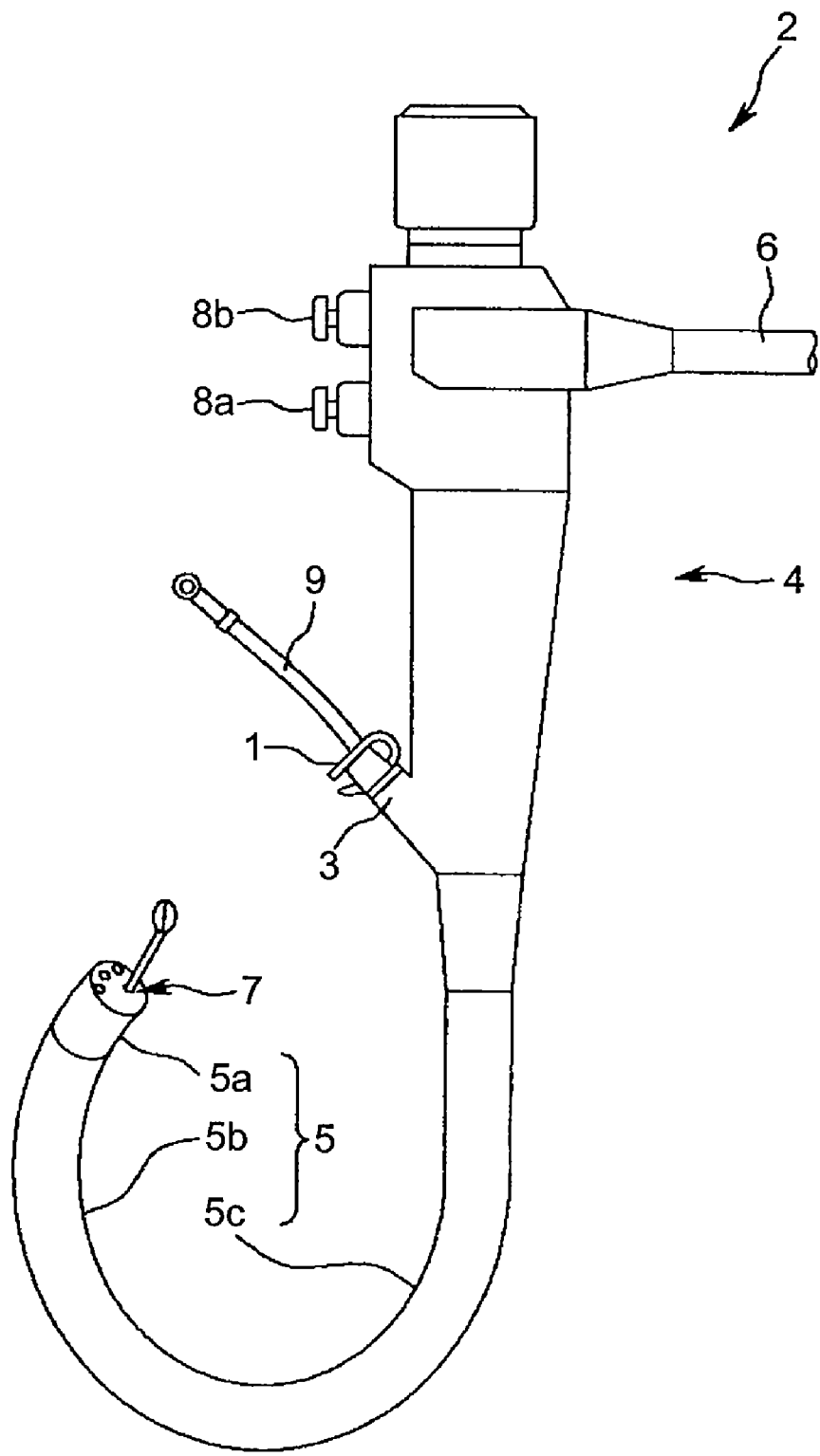
FIG. 1 is a schematic view showing an example of an endoscope to which an endoscope plug body according to a first embodiment of the invention is attached.
Figure 2:
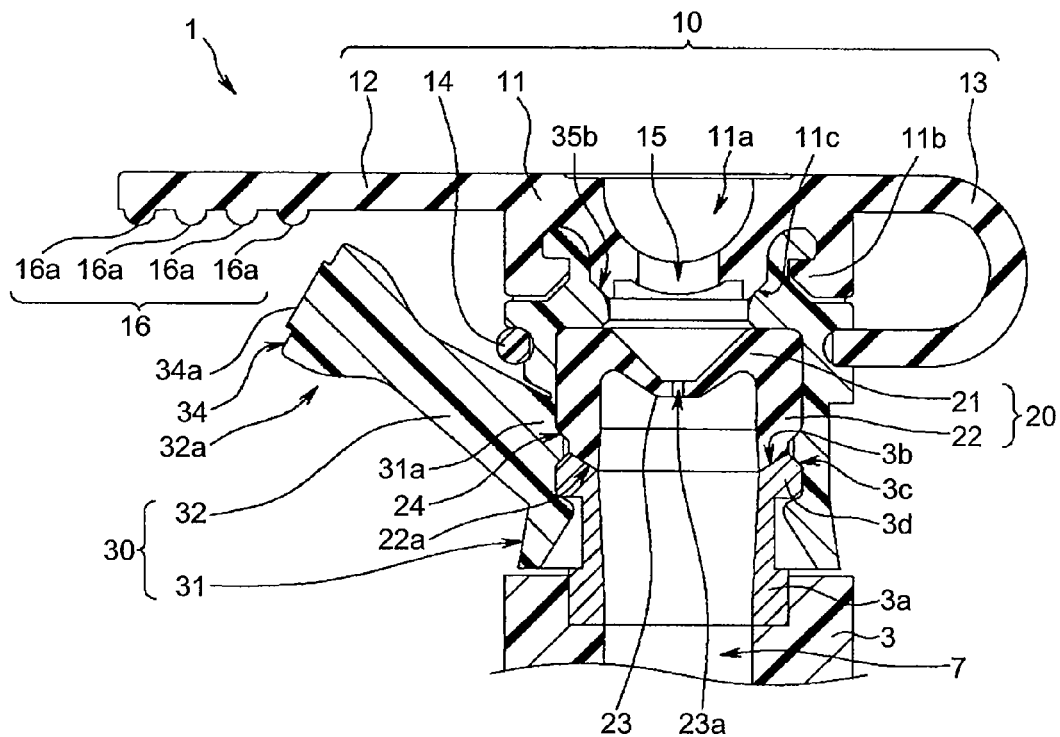
FIG. 2 is a schematic view explaining a configuration of the endoscope plug body attached to a channel opening, and is a sectional view taken along line A-A of FIG. 4.
Figure 3:
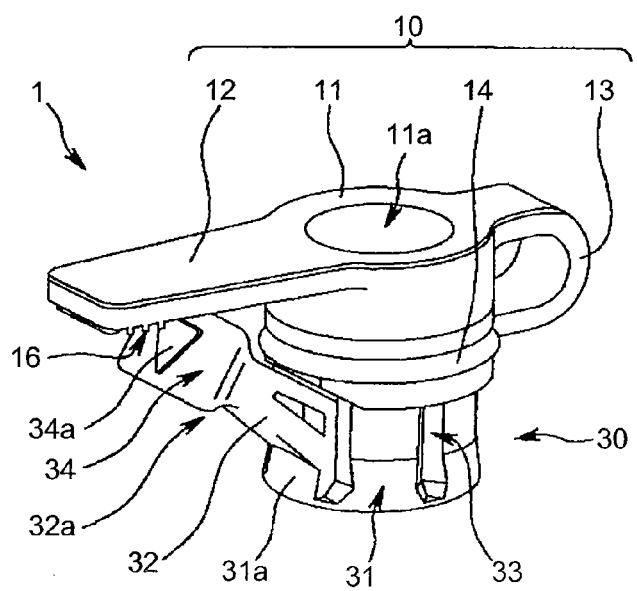
FIG. 3 is a perspective view showing an appearance of the endoscope plug body according to the first embodiment of the invention.
Figure 4:
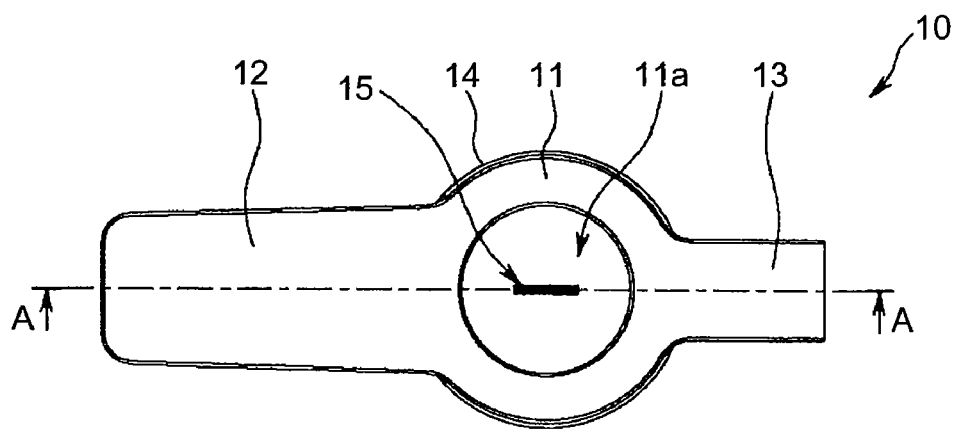
FIG. 4 is a top view showing the endoscope plug body of FIG. 3.
Figure 5:
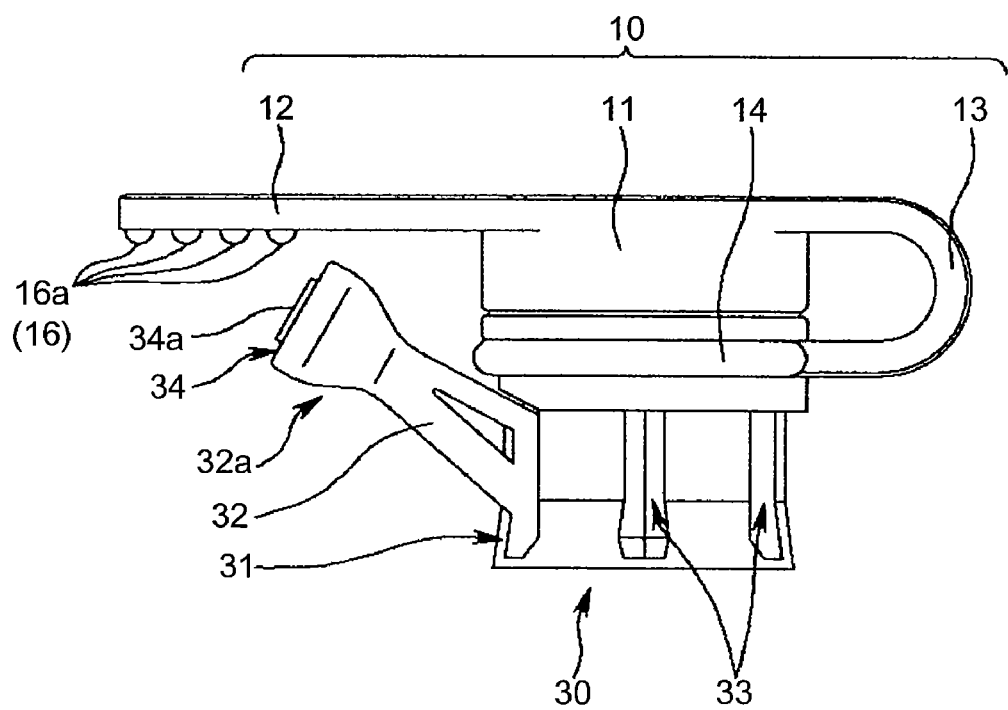
FIG. 5 is a front view showing the endoscope plug body in a state in which a protrusion shown in FIG. 3 is arranged on the left side.
Figure 6:
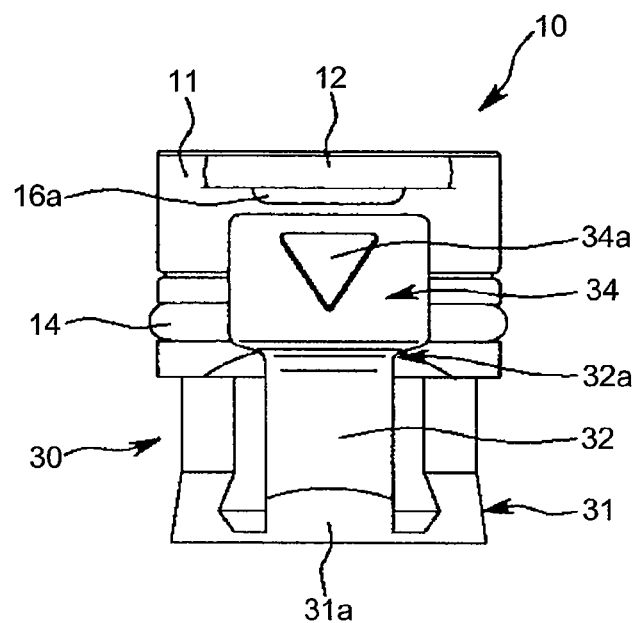
FIG. 6 is a left side view showing the endoscope plug body in a state in which the protrusion shown in FIG. 3 is arranged at the front.
Figure 7:
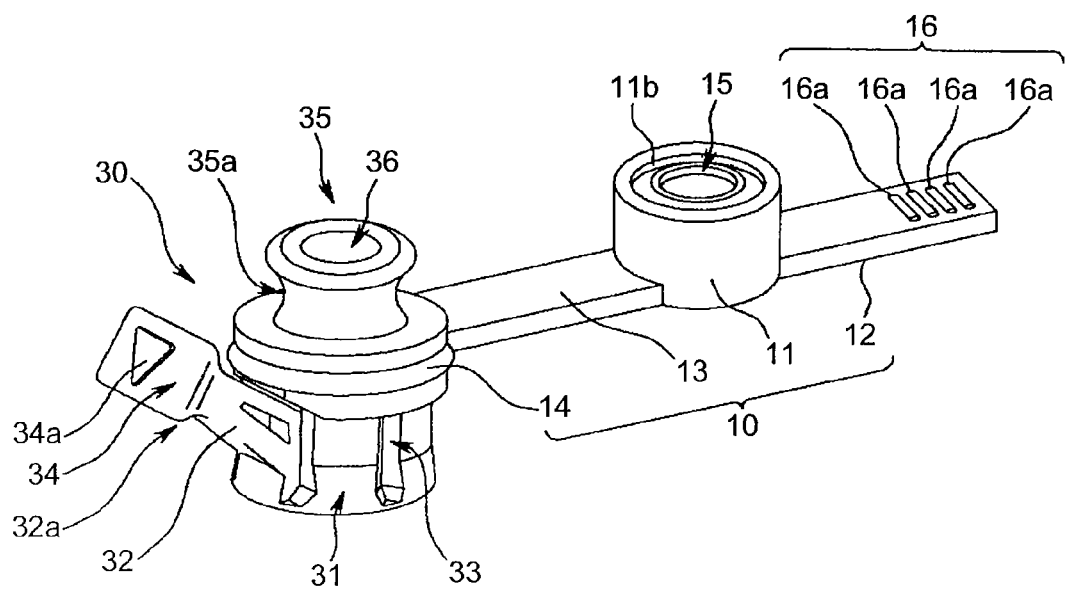
FIG. 7 is a perspective view explaining the endoscope plug body in a state in which a cap main body portion of a cap member is detached from a cap member attachment portion of a plug frame.
Figure 8:
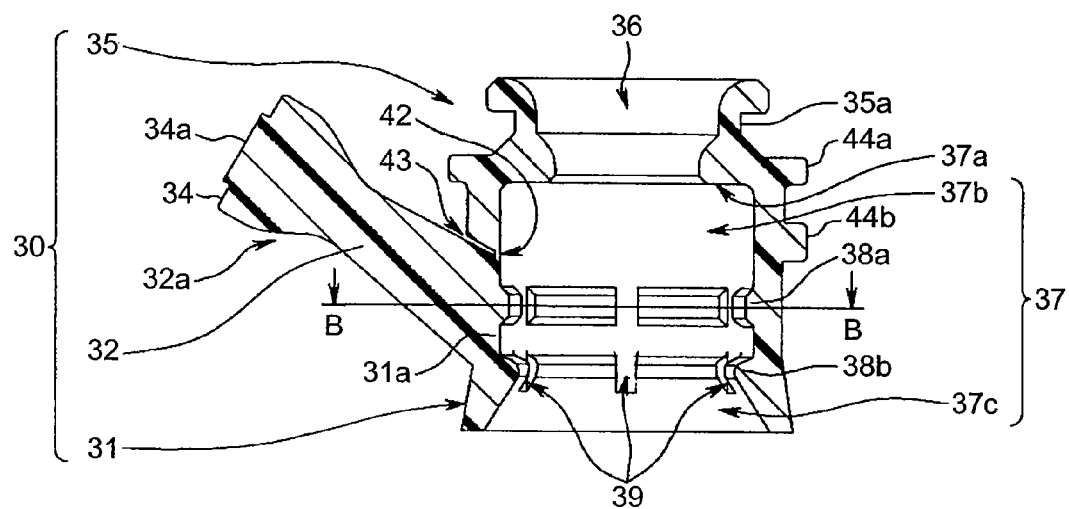
FIG. 8 is a schematic view explaining a configuration of a plug frame single body.
Figure 9:
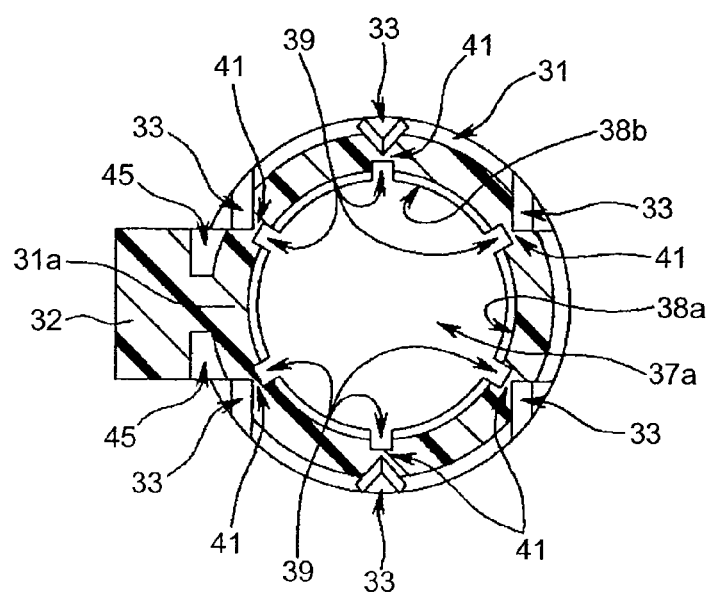
FIG. 9 is a sectional view taken along line B-B of FIG. 8.
Figure 10:
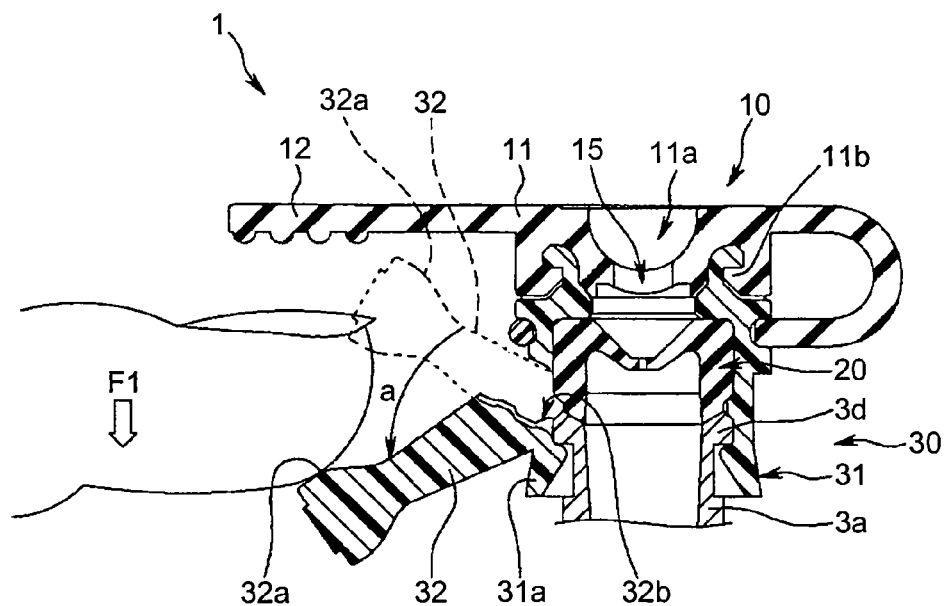
FIG. 10 is a sectional view of the endoscope plug body for explaining a primary breaking state.
Figure 11:
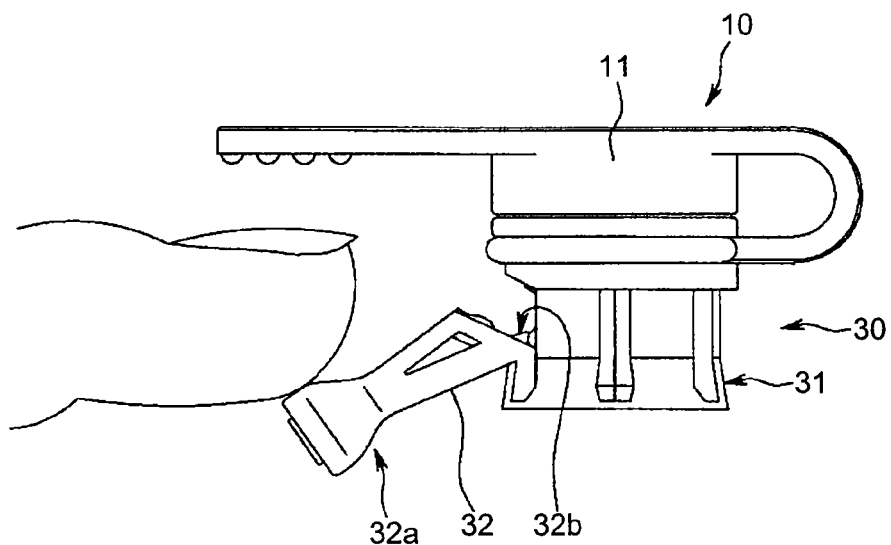
FIG. 11 is an appearance view of the endoscope plug body in the primary breaking state of FIG. 10.
Figure 12:
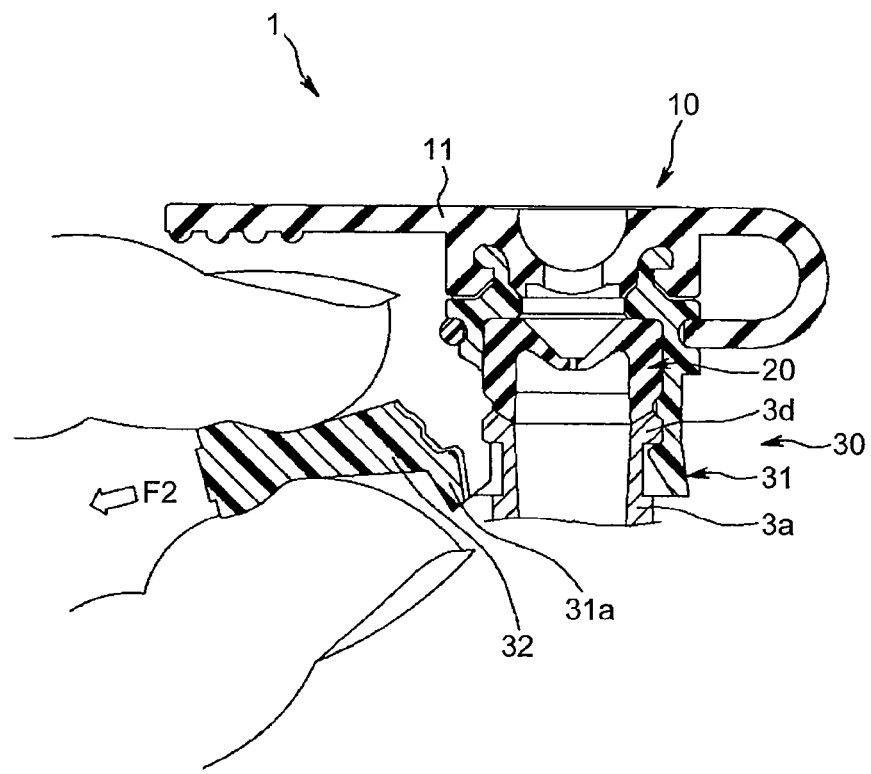
FIG. 12 is a sectional view of the endoscope plug body for explaining a secondary breaking state.
Figure 13:
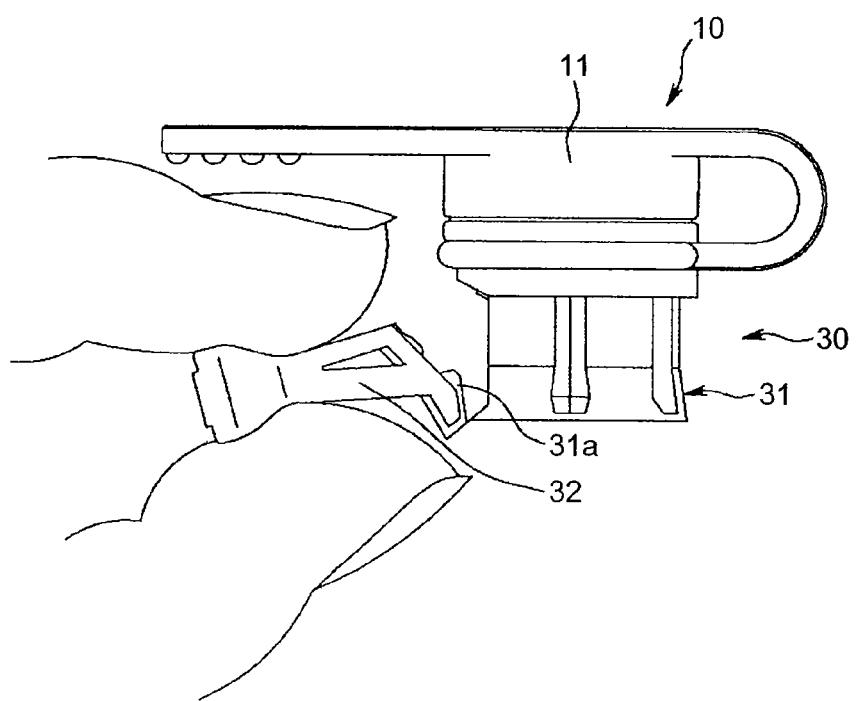
FIG. 13 is an appearance view of the endoscope plug body in the secondary breaking state of FIG. 12.
Figure 14:
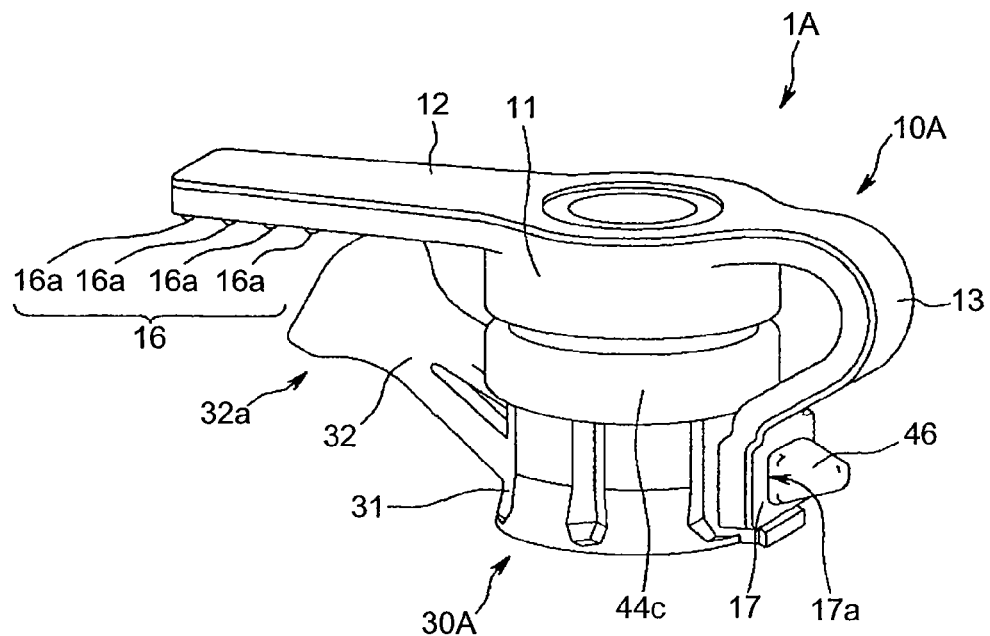
FIG. 14 is a perspective view showing an appearance of an endoscope plug body which is of a first variant of the first embodiment of the invention.
Figure 15:
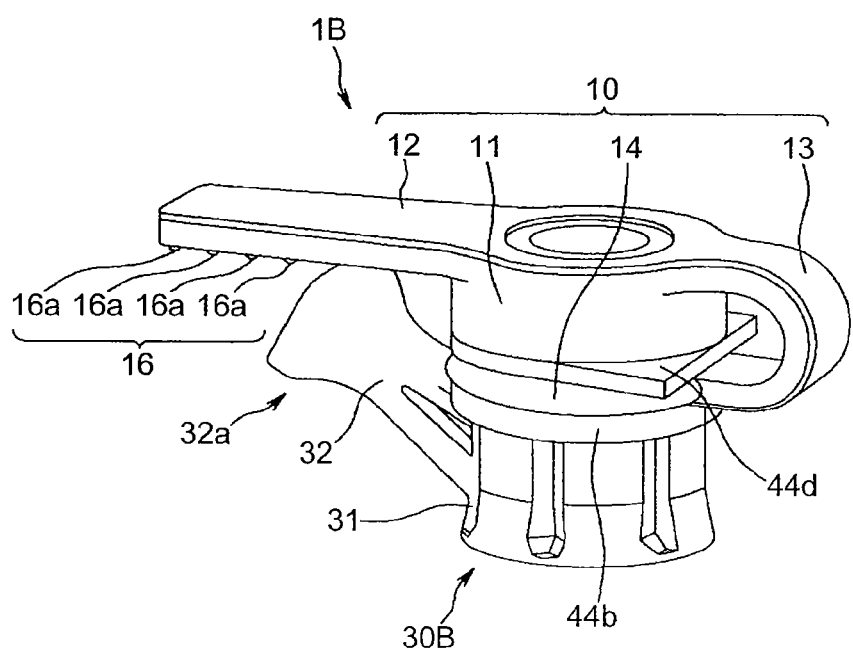
FIG. 15 is a perspective view showing an appearance of an endoscope plug body which is of a second variant of the first embodiment of the invention.

FIGS. 1 to 15 show a first embodiment of the invention. FIG. 1 is a view showing an endoscope to which an endoscope plug body is attached, FIG. 2 is a schematic view explaining a configuration of the endoscope plug body attached to a channel opening and FIG. 2 is a sectional view taken along line A-A of FIG. 4, FIG. 3 is a perspective view showing an appearance of the endoscope plug body, FIG. 4 is a top view showing the endoscope plug body of FIG. 3, FIG. 5 is a front view showing the endoscope plug body in a state in which a protrusion shown in FIG. 3 is arranged on the left side, FIG. 6 is a left side view showing the endoscope plug body in a state in which the protrusion shown in FIG. 3 is arranged at the front, FIG. 7 is a perspective view explaining the endoscope plug body in a state in which a cap main body portion of a cap member is detached from a cap member attachment portion of a plug frame, FIG. 8 is a schematic view explaining a configuration of a plug frame single body and FIG. 8 is a sectional view taken along line A-A of FIG. 4, FIG. 9 is a sectional view taken along line B-B of FIG. 8, FIG. 10 is a sectional view of the endoscope plug body for explaining a primary breaking state, FIG. 11 is an appearance view of the endoscope plug body in the primary breaking state of FIG. 10, FIG. 12 is a sectional view of the endoscope plug body for explaining a secondary breaking state, FIG. 13 is an appearance view of the endoscope plug body in the secondary breaking state of FIG. 12, FIG. 14 is a perspective view showing an appearance of an endoscope having another configuration, and FIG. 15 is a perspective view showing an appearance of an endoscope plug body having still another configuration.

As shown in FIG. 1, an endoscope plug body 1 according to the first embodiment of the invention is configured to be attached to a channel opening 3 provided in an endoscope 2. The endoscope 2 includes an operation portion 4, an insertion portion 5, and a universal cord 6. The operation portion 4 is operated while mainly grasped by an operator. The insertion portion 5 having flexibility is formed in a long and thin shape. The universal cord 6 is extended from a side portion of the operation portion 4. In the insertion portion 5, the operation portion 4 is connected to a base end side. The insertion portion 5 is formed by continuously and sequentially providing a distal end portion 5a, a bendable portion 5b, and a flexible pipe portion 5c from the front-edge side. A light guide connected to a light source device (not shown) is incorporated into the universal cord 6.

The channel opening 3 communicated with a treatment instrument insertion channel 7 is provided in the operation portion 4, and the channel opening 3 is a channel into which a treatment instrument 9 and the like are inserted. A bending operation knob (not shown), a gas-supply and water-supply button 8a, a suction button 8b, and the like are also provided in the operation portion 4. The bending operation knob remotely controls the bendable portion 5b constituting the insertion portion 5. The gas-supply and water-supply button 8a controls a gas-supply and water-supply operation through a gas-supply and water-supply channel coupled to a gas-supply and water-supply pump (not shown). The suction button 8b controls a suction operation for sucking water or a body fluid.

The endoscope plug body 1 is attached to the channel opening 3 provided in the operation portion 4. The endoscope plug body 1 is configure to secure air-tightness between the treatment instrument insertion channel 7 and the outside such that the suction operation can be performed, when the endoscope plug body 1 is attached to the channel opening 3. The endoscope plug body 1 secures the air-tightness between the inside and the outside of the treatment instrument insertion channel 7, even if the treatment instrument 9 is inserted and detached in the channel opening 3 of the treatment instrument insertion channel 7.

As described above, the insertion portion 5 has the distal end portion 5a, the bendable portion 5b, and the flexible pipe portion 5c. An observation optical system (observation optical unit, not shown), a gas-supply and water-supply nozzle (not shown), an illumination optical system (not shown), an opening of the treatment instrument insertion channel 7, and the like are provided in the distal end portion 5a. The treatment instrument insertion channel 7, which communicates a front-edge surface of the distal end portion 5a and the channel opening 3, is provided inside the insertion portion 5. Accordingly, when the treatment instrument 9 is inserted from the channel opening 3 of the operation portion 4, the front edge of the treatment instrument 9 is inserted through the inside of the treatment instrument insertion channel 7 and projected from the opening formed in the front-edge surface of the distal end portion 5a. A cable or image guide fiber, a gas-supply and water-supply channel, a suction channel, and a light guide fiber (all these components are not shown) are further provided in the insertion portion 5. These components are provided in regions from a predetermined region of the operation portion 4 to the front-edge surface of the distal end portion 5a respectively.

A configuration of the endoscope plug body 1 will be described with reference to FIGS. 2 to 9. First the configuration of the endoscope plug body 1 will be described with reference to FIG. 2. As shown in FIG. 2, the endoscope plug body 1 mainly includes a cap member 10, a plug member 20, and a plug frame 30. The plug member 20 is arranged in an internal space (the numeral 37b of FIG. 8) provided in the plug frame 30. The numeral 3a designates a venting cap. The venting cap 3a made of metal is arranged on the opening side of the channel opening 3. A through hole communicated with the treatment instrument insertion channel 7 through the channel opening 3 is formed in the venting cap 3a. A flange portion 3d having an inner inclined plane 3b and an outer inclined plane 3c is provided in a peripheral portion on the front-edge side of the venting cap 3a. The flange portion 3d is a venting cap-side latch portion. The plug frame 30 is mounted on the venting cap 3a while covering the venting cap 3d, and thereby the endoscope plug body 1 is attached to the channel opening 3.

The configuration of the plug frame 30 will be described below with reference to FIGS. 2 to 9. The plug frame 30 is formed by a resin member such as polyethylene and polypropylene having slightly elastic force, and the plug frame 30 is formed in a substantially cylindrical shape. A plug frame main body portion (hereinafter abbreviated to plug main body) 31, a protrusion 32, and a cap member attachment portion 35 are integrally provided in the plug frame 30. The plug main body 31 is attached to the venting cap 3a in the bonding state by press-fitting the plug main body 31 with elastic force having the plug frame 30.

As shown in FIGS. 3 to 7, plural V-shape grooves 33 which form later-mentioned thin portions (numeral 41 of FIG. 9) are provided at predetermined intervals in a side peripheral surface of the plug main body 31. The protrusion 32 is a plug frame breaking operation portion which is grasped by a user in breaking the plug main body 31, and the protrusion 32 constitutes a part of the breaking member. The protrusion 32 has a thickness larger than that of the plug main body 31, and the protrusion 32 is projected from a later-mentioned plug main body breaking portion 31a provided in the plug main body 31.

Specifically, the protrusion 32 is projected obliquely upward from the side peripheral surface of the plug main body 31. Pairs of V-shape grooves 33 provided in both side portions of base end portion of the protrusion 32 are formed as a notch portion which cuts and opens the plug frame 30. The front-edge side from the midpoint of the protrusion 32 is formed as a grip portion 32a which is of a support portion in operating the protrusion 32. In consideration of a grasping property of the user, the grip portion 32a is formed such that the thickness is gradually increased toward the front-edge direction. That is, the grip portion 32a is formed in a substantial pyramid shape whose vertex is formed by a plane. The front-edge surface of the grip portion 32a is formed as a plane portion 34, and an indicator 34a is formed in the plane portion 34. The indicator 34a indicates a load direction when the plug main body 31 is broken. The indicator 34a is formed in a triangular shape as in the drawings, or the indicator 34a is formed by a projection portion or recess having an arrow shape. In the first embodiment, the plug main body 31 is configured to be broken, when the user applies the load to the grip portion 32a in a downward direction of the drawings as shown by the triangular indicator 34a, in other words, when the user applies the load to the protrusion 32 in the direction in which the venting cap 3a is covered with the plug frame 30, i.e., in the plug frame fitting direction.

The cap member attachment portion 35 is formed while projected from the upper surface of the plug main body 31 by a predetermined amount, and a cap main body attaching groove 35a is provided in an outer peripheral portion of the cap member attachment portion 35. The numeral 36 designates a treatment instrument guide port. The treatment instrument guide port 36 is provided so as to face the channel opening 3, and the treatment instrument 9 and the like are inserted into the treatment instrument guide port 36.

As shown in FIG. 8, the treatment instrument guide port 36 is communicated with a space portion 37 through a top face 37a. The space portion 37 has an internal space for plug member 37b and a venting cap space 37c. The plug member 20 is arranged in the internal space for plug member 37b and the venting cap 3a is arranged in the venting cap space 37c. A ring-shape projection portion for plug member 38a and a ring-shape venting cap latching portion 38b are provided in an inner wall constituting the space portion 37. For example, the projection portion for plug member 38a is a first projection portion which is formed while having inclined surfaces on both sides of a plane portion. For example, the venting cap latching portion 38b is a second projection portion formed by two inclined surfaces, and the venting cap latching portion 38b is a plug frame-side latch portion. A vertex portion where the two inclined surfaces of the venting cap latching portion 38b abut on is formed by a flat surface or a smoothly curved surface. The flange portion 3d is latched along the outer periphery of the venting cap 3a, which allows the venting cap latching portion 38b to function as an example of the latch member. The latch member attaches the plug frame 30 to the venting cap 3a. The venting cap latching portion 38b is located in the base end portion of the protrusion 32, and the venting cap latching portion 38b is arranged at the position where the venting cap latching portion 38b engages the flange portion 3d of the venting cap 3a which is mounted inside the space portion 37.

The inclined surface located on a space opening side forming the projection portion for plug member 38a is configured to abut on the outer inclined plane 3c of the venting cap 3a. A projection amount of projection portion for plug member 38a is set such that the plug member 20 arranged in the internal space for plug member 37b is prevented from dropping out from the internal space for plug member 37b.

As shown in FIG. 9, recesses 39 which face the V-shape grooves 33 respectively are provided in an inner wall surface of the space portion 37. Therefore, first thin portions 41 formed by the V-shape groove 33 and the recess 39 are provided in the plug main body 31. The thickness between the first thin portion 41 and an opening end of the plug main body 31 is formed while equal to or slightly larger than the thickness of the thin portion 41. The first thin portion 41 is formed by forming the V-shape groove 33 and the recess 39 in the plug main body 31 to reduce the plug main body 31, and the first thin portion 41 functions as an example of the broken portion which is of an area where the rupture strength is weakened compared with other areas of the plug main body 31. The broken portion is an area which is torn off when the later-mentioned plug main body breaking portion 31a is broken by separating the plug main body breaking portion 31a from plug frame 30. Therefore, the broken portion traverses the venting cap latching portion 38b along the side of the plug main body breaking portion 31a, and the broken portion is formed in the area reaching one end portion (for example, an end portion where the venting cap space 37a is formed) of the plug frame 30, and the rupture strength may be weakened compared with other areas of the plug main body 31 in the broken portion. In this case, for example, the broken portion may be formed by reducing the thickness of the plug main body 31 like the first thin portion 41, and the broken portion may be formed in a perforation where through holes are intermittently made to weaken the rupture strength in the area. As shown in FIG. 9, the protrusion 32 is integrally provided between the first thin portions 41 constituting the plug main body 31.

As shown in FIGS. 8 and 9, a groove 43 is provided in the outer peripheral surface of the plug main body 31 and in the upper-surface side portion of the protrusion 32. The groove 43 extended in the circumferential direction and the groove 43 constitutes a second thin portion 42. As with the first thin portion 41, the second thin portion 42 functions as an example of the broken portion which is of an area where the rupture strength. The second thin portions 42 are configured to be connected to the first thin portions 41 provided in both side surfaces of the protrusion 32 respectively. Specifically, the second thin portion 42 is continued to the first thin portion 41 which is formed along the side of the first thin portion 41 while traversing the venting cap latching portion 38b, and the second thin portion 42 is formed in the direction perpendicular to or oblique to the direction in which the first thin portion 41 is formed. Therefore, in the plug main body 31, a portion formed by connecting the first thin portion 41 and the second thin portion 42 constitutes the plug main body breaking portion 31a which is of an example of the breaking member. That is, the plug main body breaking portion 31a is an area which is surrounded by the first thin portion 41 and the second thin portion 42, and the plug main body breaking portion 31a is an area which reaches one end portion of the plug frame 30 and a partial area of the plug frame 30 whose inner wall surface includes a part of the latch portion of the venting cap latching portion 38*b* which latches the venting cap 3*a* fitted in the venting cap space 37*c*. As with the first thin portion 41, the second thin portion 42 may be formed by reducing the thickness of the plug main body 31, and the broken portion may be formed in the perforation where through holes are intermittently made to weaken the rupture strength in the area.

An annular first flange 44*a* and an annular second flange 44*b* are provided on the upper surface side of the plug main body 31. The first flange 44*a* and the second flange 44*b* are the groove portion and the fitting portion, where a ring portion (see the numeral 14 of FIG. 7) is arranged. The ring portion constitutes a base-end side portion included in the cap member 10. The second flange 44*b* is formed in the annular shape while a part of the second flange 44*b* is lacked in a neighbor on the side of the protrusion 32 in order to prevent interference with the protrusion 32.

The numeral 45 designates a notch portion for preventing a shrinkage cavity. In the plug frame 30, because the thickness of the protrusion 32 is larger than the thicknesses of the plug main body 31 and cap member attachment portion 35, the shrinkage cavity is generated in the protrusion 32, which results in a risk of not obtaining the desired shape. A flow of resin melted during molding is improved by providing the notch portion 45 for preventing the shrinkage cavity, which obtains the protrusion 32 whose thickness has the desired rigidity.

As shown in FIG. 2, the cylindrical plug member 20 is formed by an elastic member such as silicone rubber, butyl rubber, and natural rubber. The plug member 20 is formed in a predetermined diameter and height so as to be accommodated in the internal space for plug member 37*b*.

The plug member 20 includes a bottom forming portion 21 and an outer periphery forming portion 22. One surface side of the bottom forming portion (hereinafter abbreviated to bottom) 21 abuts on the ceiling surface 37*a*. The outer periphery forming portion (hereinafter abbreviated to outer peripheral portion) 22 is projected from the bottom portion 21. A front-edge slope 22*a* is provided in a front-edge surface of the outer peripheral portion 22. The front-edge slope 22*a* is configured such that the inner inclined plane 3*b* provided in the venting cap 3*a* abuts on the front-edge slope 22*a*.

A boundary portion 23 is provided in a central portion of the bottom portion 21. The boundary portion 23 is formed in the concave shape when viewed from one side, and the boundary portion 23 is formed in a projected shape when viewed from the opening side of the outer peripheral portion 22. The thickness of the boundary portion 23 is reduced compared with the thickness of the outer peripheral portion 22, and thereby the boundary portion 23 is configured to be easily elastically deformed. A treatment instrument inserting round hole (hereinafter abbreviated to round hole) 23*a* is made in the central portion of the boundary portion 23. The round hole 23*a* is a second treatment instrument insertion portion into which the treatment instrument 9 and the like can be inserted. The diameter of the round hole 23*a* is formed smaller than the outer diameter of the treatment instrument 9, to be inserted into the round hole 23*a*, by a predetermined amount. Accordingly, in the state in which the treatment instrument 9 or the like is inserted into the round hole 23*a*, the inner peripheral surface of the round hole 23*a* comes into close contact with the outer peripheral surface of the treatment instrument 9 by elastic force possessed by the plug member 20, and thereby the watertight and airtight state can be retained. When the treatment instrument 9 is inserted into the round hole 23*a*, the shape of the outer peripheral portion 22 is not changed, but only the boundary portion 23 whose thickness is reduced is deformed, and the shape of the plug member 20 is maintained. The numeral 24 designates a retaining slope. The inclined surface provided on the side of the internal space for plug member 37*b* of the projection portion for plug member 38*a* abuts on the retaining slope 24.

As shown in FIGS. 2 to 7, the cap member 10 is formed by an elastic member such as the silicone rubber, the butyl rubber, and the natural rubber. A cap main body portion 11, a tongue portion 12, a coupling portion 13, and a ring portion 14 which are of a cap portion are integrally provided in the cap member 10.

The cap main body portion 11 is formed in the substantially cylindrical shape. A hemispherical recess 11*a* is provided in the substantially central portion of the cap main body portion 11. A treatment instrument inserting slit (hereinafter abbreviated to slit) 15 is formed in a bottom of the hemispherical recess 11*a*. The slit 15 is the first treatment instrument insertion portion into which the treatment instrument 9 or the like can be inserted. In a non-insertion state in which the treatment instrument 9 or the like is not inserted the slit 15, the slit 15 becomes the close contact state by the elastic force possessed by the cap member 10, and the slit 15 retains the watertight and airtight state. On the other hand, in the insertion state in which the treatment instrument 9 or the like is inserted the slit 15, the inner peripheral surface of the slit 15 is brought into close contact with the outer peripheral surface of the treatment instrument 9 by the elastic force possessed by the cap member 10, and the slit 15 retains the watertight and airtight state. A circumferential protrusion 11*b* is provided in the cap main body portion 11, and the protrusion 11*b* is press-fitted in the cap main body attaching groove 35*a* provided in the cap member attachment portion 35 of the plug frame 30.

The tongue portion 12 is one which is grasped by the user when the user opens and closes the treatment instrument guide port 36 using the cap member 10. The tongue portion 12 is provided while projected by a predetermined amount from the outer-peripheral side face of the cap main body portion 11 toward one direction so as to be continued to the upper surface of the cap main body portion 11. Specifically, the tongue portion 12 is formed such that the front edge is located far way from the plane portion 34 in the state in which the tongue portion 12 passes above the protrusion 32 projected from the plug main body 31. A slip resistance portion 16 is provided in the front-edge-side lower surface in the drawings which is located on the side of the protrusion 32 of the tongue portion 12. The slip resistance portion 16 prevents the fingers of the user who grasps the tongue portion 12 from slipping in opening and closing the cap member 10. For example, the slip resistance portion 16 is formed by plural protrusions 16*a*. Because the tongue portion 12 is formed by an elastic member, the tongue portion 12 does not prevent the user from grasping the grip portion 32*a* or from operating the protrusion 32, even if the tongue portion 12 is located near the protrusion 32 as shown in FIG. 2. The tongue portion 12 may be made of a hard resin such as plastic. In this case, it is necessary that the hard tongue portion 12 be arranged away from the protrusion 32 so as not to come into contact with a column extended from the plane portion 34 toward the projected direction of the protrusion 32.

The coupling portion 13 is projected by a predetermined amount from the outer-peripheral side face of the cap main body portion 11 toward the other direction such that the coupling portion 13 is continued to the upper surface of the cap main body portion 11 while arranged on a substantially straight line. The coupling portion 13 is formed in a belt shape with a constant thickness. A ring portion 14 formed in an annular shape is provided in an end face of the coupling portion 13. The ring portion 14 is formed in a circular shape, a rectangular shape, and the like in cross section. The ring portion 14 is press-fitted in a ring attachment portion provided in the plug main body 31.

The cap main body portion 11 has a front-edge abutting face 11c, and the cap member attachment portion 35 has an inner-periphery abutting face 35b. The front-edge abutting face 11c and the inner-periphery abutting face 35b are in close contact with each other in the state in which the circumferential protrusion 11b of the cap main body portion 11 is attached to the cap main body portion press-fitted in the cap main body attaching groove 35a provided in the cap member attachment portion 35, and thereby the watertight and airtight state is retained between the cap member 10 and the plug frame 30. The outer diameter of the cap main body portion 11 is substantially equal to the outer diameter of the first flange 44a.

A procedure of assembling the endoscope plug body 1 will be described below. The plug member 20 is accommodated and arranged in the internal space for plug member 37b of the plug frame 30. At this point, the plug member 20 is elastically deformed. The projection portion for plug member 38a of the plug frame 30 abuts on the retaining slope 24 of the plug member 20 to prevent the plug member 20 from dropping out from the inside of the internal space for plug member 37b.

Then, the ring portion 14 of the cap member 10 is press-fitted in the ring attachment portion which is formed by the first flange 44a and the second flange 44b. Then, as shown in FIG. 3 and the like, the circumferential protrusion 11b provided in the cap main body portion 11 of the cap member 10 is fitted in the cap main body attaching groove 35a provided in the cap member attachment portion 35 of the plug frame 30. The endoscope plug body 1 shown in FIG. 7 is assembled through the above procedure. The endoscope plug body 1 in the assembled state is supplied to the user.

Then, the attachment of the endoscope plug body 1 to the channel opening 3 will be described. In order to attach the endoscope plug body 1 to the channel opening 3, the opening side which is of one end portion of the plug main body 31 of the plug frame 30 is fitted in the venting cap 3a such that the venting cap 3a is covered from a predetermined fitting direction. Then, the venting cap latching portion 38b and each thin portion 41 which are provided in the plug main body 31 surmount the flange portion 3d while elastically deformed. Therefore, the venting cap latching portion 38b is latched and arranged in the flange portion 3d while coming into close contact with the flange portion 3d. At this point, the venting cap 3a is arranged in the venting cap space 37c, and the inner inclined plane 3b of the venting cap 3a abuts on the front-edge slope 22a of the plug member 20 accommodated in the internal space for plug member 37b. This enables the plug member 20 to be moved toward the side of ceiling surface 37a, and the inner inclined plane 3b and the front-edge slope 22a come into close contact with each other while the bottom portion 21 comes into close contact with the ceiling surface 37a. Therefore, the endoscope plug body 1 retains the channel opening 3 in the watertight and airtight state from the outside.

In this arrangement, when the load is applied to the plug main body 31 in the swing manner by causing the projection portion for plug member 38a to abut on the outer inclined plane 3c, because the flange portion 3d is clamped and fixed by the projection portion for plug member 38a and the venting cap latching portion 38b, the attachment state of the endoscope plug body 1 to the channel opening 3 is stabilized. In other words, when the load is applied to the plug main body 31 in the swing manner, the plug frame 30 is arranged in the channel opening 3 while hardly falls with respect to the channel opening 3.

In the state in which the endoscope plug body 1 is attached to the channel opening 3, in inserting the treatment instrument 9 or the like, the treatment instrument 9 is introduced into the channel opening 3 through the hemispherical recess 11a, the slit 15, and the round hole 23a. In this treatment instrument insertion state, the inner peripheral surface of the round hole 23a comes into substantially close contact with the outer peripheral surface of the treatment instrument 9 by the elastic force possessed by the plug member 20. A part of the inner peripheral surface of the slit 15 also comes into close contact with the outer peripheral surface of the treatment instrument 9 by the elastic force possessed by the cap member 10. That is, in the state in which the treatment instrument 9 is introduced into the channel opening 3 through the endoscope plug body 1, a part of the inner peripheral surface of the slit 15 and the inner peripheral surface of the round hole 23a come into close contact with the outer peripheral surface of the treatment instrument 9. Accordingly, the endoscope plug body 1 prevents the body fluid and the filth from flying out to the outside when the treatment instrument 9 is inserted through the endoscope plug body 1.

In the case where the treatment instrument having a large outer diameter is inserted into the endoscope plug body 1, the treatment instrument may be inserted while the cap main body portion 11 of the cap member 10 is detached from the cap member attachment portion 35 of the plug frame 30. Therefore, an insertion capacity for inserting the treatment instrument is decreased. The inner peripheral surface of the round hole 23a comes into close contact with the outer peripheral surface of the treatment instrument by the elastic force possessed by the plug member 20, which allows the watertight and airtight state to be maintained.

Then, the detachment of the endoscope plug body 1 from the channel opening 3 will be described. In detaching the endoscope plug body 1 attached to the channel opening 3, while the continued state of the plug frame 30 in the circumferential direction is maintained, a part of the plug main body 31 is broken, specifically the plug main body breaking portion 31a which is of a part of the plug main body 31 is broken. At this point, as shown in FIG. 10, for example, the user put a forefinger on the upper surface of the grip portion 32a of the protrusion 32. When the tongue portion 12 obstructs the forefinger, the tongue portion 12 is moved by a nail side so as to be lifted. The load in the downward direction indicated by an arrow F1, i.e., the load in the direction in which the endoscope plug body 1 is fitted (namely, in the direction in which the venting cap 3a is covered with the plug body 30) is applied to the protrusion 32. Then, the protrusion 32 is rotated by the applied load in the direction indicated by an arrow a about a portion (for example, a part of the flange portion 3d which is in contact with the venting cap latching portion 38b) where the venting cap latching portion 38b and the flange portion 3d are brought into contact with each other. At this point, stress generated by the protrusion 32 is concentrated on the second thin portion 42 and first thin portion 41 which are located near the protrusion 32. The venting cap 3a has a high rigidity because the venting cap 3a is made of metal. Accordingly, the plug main body 31 is prevented from being crushed inward to disperse the load while the flange portion 3d of the venting cap 3a is not crushed.

The second thin portion 42 provided in the upper-surface side portion of the protrusion 32 is broken by the stress generated by the protrusion 32. Then, the first thin portions 41 provided in both the end portions of the plug main body breaking portion 31a in which the protrusion 32 is integrally provided are broken from the sides of the second thin portions 42. At this point, the plug main body breaking portion 31a in which the protrusion 32 is integrally provided is not completely separated from the plug main body 31, namely, a part of the plug main body breaking portion 31a is still connected to the plug main body 31 by a predetermined amount. Accordingly, as shown in FIG. 11, a base portion 32a of the protrusion 32 is folded down in the seeming breaking state of the plug main body 31. This breaking state is referred to as primary breaking state.

After the primary breakage, as shown in FIGS. 12 and 13, for example, the user grasps the grip portion 32a of the protrusion 32 with the forefinger and a thumb. Then, the load is applied to the protrusion 32 in an obliquely downward direction as shown by an arrow F2. Therefore, the first thin portion 41 which is not completely broken by the primary breakage is completely broken, which brings in the breaking completion state in which the plug main body breaking portion 31a and the protrusion 32 are completely broken while separated from the plug main body 31. This breaking state is referred to as secondary breaking state. As described above, the protrusion 32 functions as the operation portion which tears off the first thin portion 41 and second thin portion 42 to separate the plug main body breaking portion 31a from the plug main body 31. Thus, the first thin portion 41 and second thin portion 42 are torn off to separate the plug main body breaking portion 31a from the plug frame 30 (specifically, plug main body 31) by operating the protrusion 32, which partially breaks the latch portion of the venting cap latching portion 38b latched in the flange 3d. In this case, in the plug frame 30, the area continued in the circumferential direction, e.g., the cap member attachment portion 35 is not broken but the shape of the cap member attachment portion 35 is maintained, so that the continued state is maintained in the circumferential direction. In the continued state in the circumferential direction of the plug frame 30, for example, the cap member attachment portion 35 suppresses the expansion of the cylindrical plug frame 30. The endoscope plug body 1 in which the plug main body breaking portion 31a and protrusion 32 are separated from the plug main body 31 is still attached to the channel opening 3 in the secondary breaking state. In this case, because the continued state in the circumferential direction is maintained in the plug frame 30 in the secondary breaking state, the cylindrical shape which is detachably attached to the venting cap 3a can be maintained to prevent the plug main body 31 from unintentionally dropping out from the venting cap 3a. Furthermore, because the protrusion 32 is broken by pulling the protrusion 32 toward the channel opening 3 (i.e., toward the direction in which the plug frame 30 abuts on the venting cap 3a), the force is not applied in the direction in which the plug main body 31 is separated from the channel opening 3 (i.e., in the direction in which the plug main body 31 drops out from the venting cap 3a), and the plug main body 31 does not drop out from the venting cap 3a.

Then, the endoscope plug body 1 which is still attached to the channel opening 3 is detached. At this point, while the plug main body breaking portion 31a is separated from the plug main body 31, the plural first thin portions 41 are provided in the plug main body 31, which allows the cylindrical shape of the plug frame 30 to be deformed so as to be able to withdraw from the venting cap 3a. Accordingly, the latched state between the plug frame 30 and the venting cap 3a is easily released by the user's hand, and the endoscope plug body 1 is smoothly detached from the channel opening 3.

Thus, the plug main body breaking portion configured to provide the broken portion such as the thin portion where the rupture strength is weakened is provided in a part of the plug main body included in the plug frame constituting the endoscope plug body, and the protrusion is provided in the plug main body breaking portion to appropriately operate the protrusion. Therefore, the plug main body breaking portion can be separated from the plug main body with the small capacity while the endoscope plug body does not drop out from the channel opening.

This enables the endoscope plug body from which a part of the plug main body is separated to be smoothly detached from the channel opening using the hand of the user. Because it is judge from the appearance whether or not the plug main body breaking portion which is of a part of the plug main body is broken, the working mistake that the used endoscope plug body is wrongly reused can securely be prevented. Accordingly, the new endoscope plug frame is attached to the channel opening in each case.

The load for downwardly pressing the protrusion is applied to perform the primary breakage to a part of the plug main body, namely, the finger is moved onto the operation portion side of the endoscope to perform the primary breakage to a part of the plug main body, so that the finger can be prevented from hitting the neighbor with great force when the finger slips from the protrusion by releasing the load of the fingertip at a burst.

The plug main body has the structure in which the plug main body breaking portion provided in the frame body is broken in two stages, a primary breaking state and a secondary breaking state. Therefore, the protrusion is connected to the plug main body at the time of completion of the primary breakage in which the large load is applied, so that the protrusion can be prevented from solely dropping out.

Because only a part of the side face of the plug main body is broken, in the secondary breaking state, the plug main body can be retained in the channel opening while substantially confined within an original form as the structure. Accordingly, the plug member to which the body fluid and filth adhere is prevented from dropping out to hygienically perform the working.

Because the grip portion of the protrusion is formed in the pyramid shape, the protrusion can be pulled in such a manner that the fingers are put on the protrusion while the protrusion is vertically or horizontally clamped between the fingers. Therefore, the load is easily applied, and the secondary breakage can be easily performed.

The breaking operation can also be performed by putting the thumb on the protrusion while another finger is put on the operation portion. In this case, the workability is improved because the breaking operation is performed with one hand.

Because the protrusion is projected upward in the cap direction, the protrusion can be moved only in the downward direction, i.e., only in the channel opening direction, and the force cannot be applied in the direction in which the plug body drops out from the channel opening.

The endoscope plug body may be configured as shown in FIG. 14. FIG. 14 is a perspective view schematically showing an appearance of an endoscope plug body which is of a first variant of the first embodiment of the invention. A medical endoscope plug body 1A shown in FIG. 14 differs from the endoscope plug body of the first embodiment in configurations of the cap member attachment portion in a plug frame 30A and the ring portion of the cap member. That is, as shown in FIG. 14, an arrow-head shape portion 46 which is of the fitting portion is formed in the side-face lower portion on the side opposite to the side on which the protrusion 32 of the plug frame 30A of the endoscope plug body 1A is formed. The arrow-head shape portion 46 is formed in the rectangular shape, the arrow-head shape portion 46 is enlarged toward the based end side, and the arrow-head shape portion is formed in a thin square pole in the lowermost portion on the base end side. A flat portion 17 which is of a base-end side portion is formed in a cap member 10A while being integral with the coupling portion 13. A square hole 17a having the same size as the square pole is formed in the substantial center of the flat portion 17, and the square hole 17a is attached after the square hole 17a is elastically deformed along the arrow-head shape portion 46. In the plug main body 31 of the plug frame 30A, unlike the first embodiment, the first flange 44a is not distinguished from the second flange 44b, but one flange portion 44c is formed. Because other configurations are similar to those of the first embodiment, the same component is designated by the same numeral and the description will not be repeated.

Thus, because the ring portion does not exist in the cap member 10A, when the endoscope plug body 1A is assembled by an automatic machine, the components such as the cap member 10A can be prevented from intertwining with one another and components are easily arranged in a parts feeder. Accordingly, the same effect as the first embodiment is obtained in the first variant, and the first variant is suitable to large-scale production with the automatic machines, which leads to the cost reduction.

The endoscope plug body may be configured as shown in FIG. 15. FIG. 15 is a perspective view schematically showing an appearance of an endoscope plug body which is of a second variant of the first embodiment of the invention. In an endoscope plug body 1B shown in FIG. 15, a retaining fin 44d which constitutes the fitting portion is provided in the first flange 44a. Therefore, the same effect as the first embodiment is obtained in the second variant. When the cap main body portion 11 is detached from the cap member attachment portion 35 and pulled hard upward, because the retaining fin 44d is provided, the ring portion 14 is hooked by the retaining fin 44d, the cap member 10 is not carelessly separated from a plug frame 30B, and the cap main body portion 11 is easily opened and closed.

Figure 16:
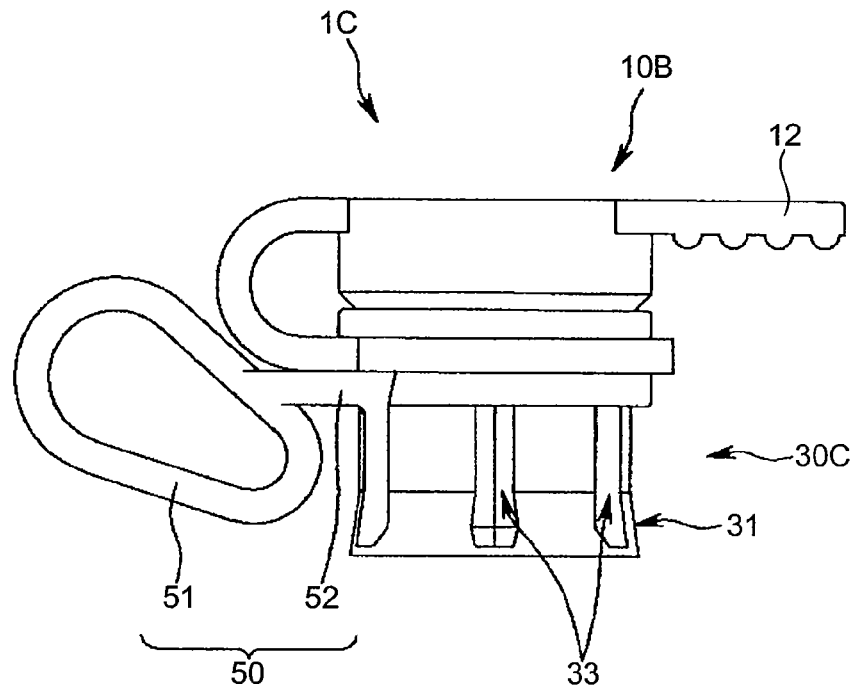
FIG. 16 is a view showing an endoscope plug body according to a second embodiment of the invention which includes a plug frame having a plug main body breaking ring.
Figure 17:
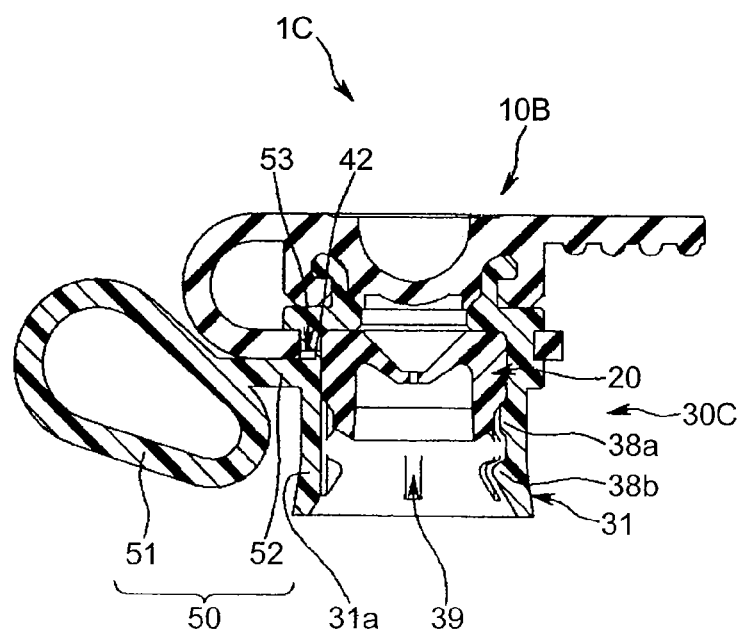
FIG. 17 is a sectional view explaining a configuration of the endoscope plug body according to the second embodiment of the invention.
Figure 18:
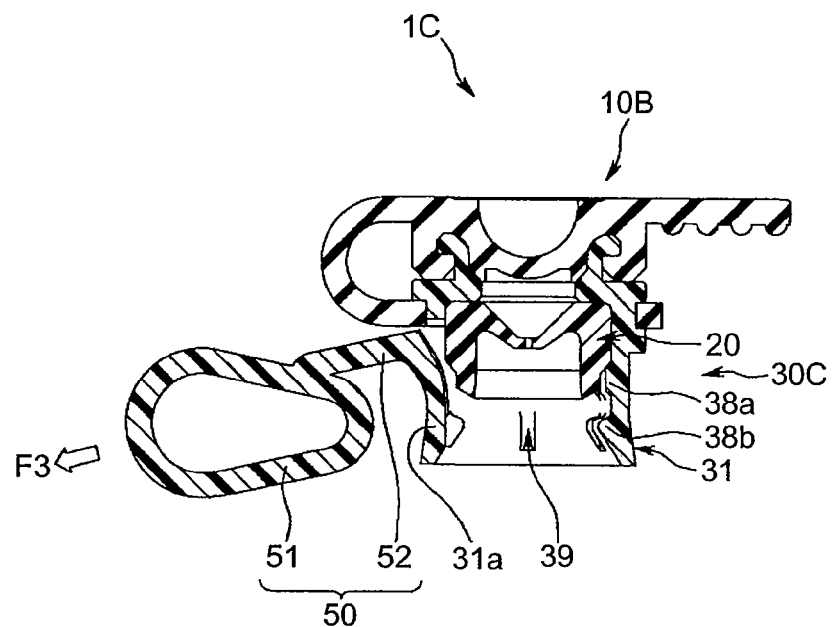
FIG. 18 is a view showing a state in which a load is applied to the plug main body breaking ring to break a plug main body breaking portion.
Figure 19:
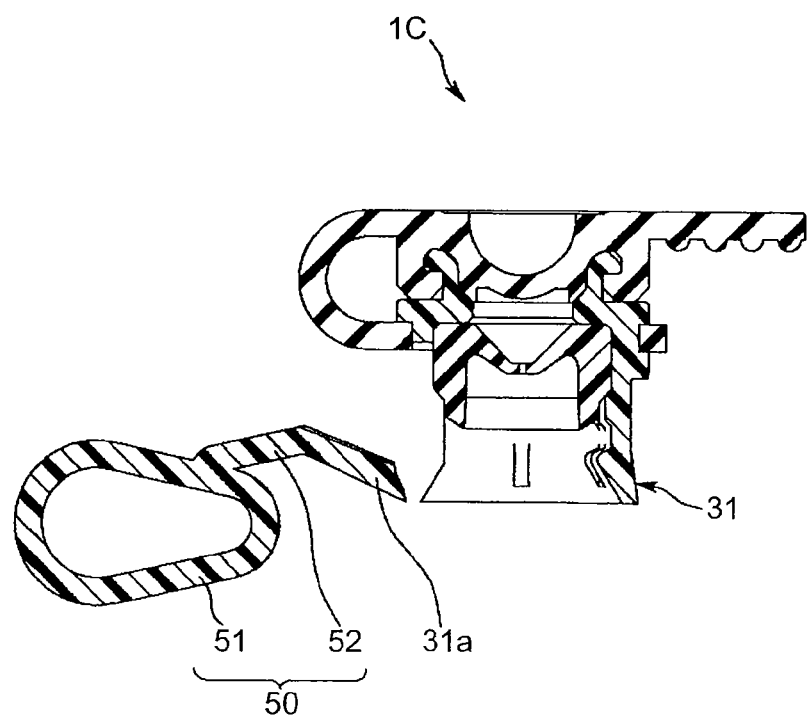
FIG. 19 is a view showing a breaking completion state in which a part of the plug main body is broken.

An endoscope plug body according to a second embodiment of the invention will be described below. FIGS. 16 to 19 show the second embodiment of the invention. FIG. 16 is a view showing the endoscope plug body which includes a plug frame having a plug main body breaking ring, FIG. 17 is a sectional view explaining a configuration of the endoscope plug body, FIG. 18 is a view showing a state in which a load is applied to the plug main body breaking ring to break a plug main body breaking portion, and FIG. 19 is a view showing a breaking completion state in which a part of the plug main body is broken.

For a plug frame 30C, an endoscope plug body 1C according to the second embodiment of the invention has the same configuration as the first embodiment with some exceptions. For a cap member 10B, the tongue portion 12 is shorter compared with that of the first embodiment, and the ring portion 14 has a rectangular shape in cross section. As shown in FIGS. 16 and 17, the plug frame 30C of the second embodiment differs from the plug frame of the first embodiment in the configuration corresponding to the protrusion 32 and the configuration surrounding the thereof. Specifically, in the plug frame 30C, a plug main body breaking ring portion 50 as the plug frame breaking operation portion is provided while being integral with the plug main body breaking portion 31a in place of the protrusion 32.

The plug main body breaking ring portion 50 includes a ring portion 51 on which the user can put the finger or the like and a belt-shape coupling portion 52. The coupling portion 52 is integral with the ring portion 51. The coupling portion 52 is projected toward the right horizontal direction from a mid portion of the plug main body breaking portion 31a provided in the plug main body 31.

In the second embodiment, as with the first embodiment, the first thin portions 41 are formed in both the side portions in the coupling portion with the plug main body 31 of the coupling portion 52. A notch 53 is provided above the coupling portion 52. The notch 53 is formed to the first thin portions 41 which are of the side portions. The thickness of the coupling portion 52 is configured so as not to be cut even if the plug main body breaking ring portion 50 is pulled toward the direction of an arrow F3 with the predetermined load. The notch 53 is formed in position in order to concentrate the stress on the neighbor of the base portion of the coupling portion 52.

In the second embodiment, the tongue portion 12 of the cap member 10B is prevented from interfering with the ring portion 51 of the plug main body breaking ring portion 50. Therefore, the attachment position of the tongue portion 12 is changed with respect to the plug frame 30C of the cap member 10B such that the tongue portion 12 is located at the position where the tongue portion 12 faces the ring portion 51 across a center axis of the plug frame 30C. Because other configurations are similar to those of the first embodiment, the same component is designated by the same numeral and the description will not be repeated.

In the second embodiment, when the endoscope plug body 1C is detached from the channel opening 3, the user put the finger on the ring portion 51 of the plug main body breaking ring portion 50. Then, the plug main body breaking ring portion 50 is pulled with a load F3 in the arrow direction (for example, the direction in which the plug main body 31 abuts on the venting cap 3a). Therefore, the load is concentrated on the upper end of the first thin portion 41 in the upper-end base of the coupling portion 52 in which the notch 53 is provided. The load F3 is continuously applied while the finger is put on the ring portion 51, which results in the primary breaking state. Then, the load which is smaller than the load F3 is continuously applied. Therefore, the breakage of the first thin portion 41 proceeds to obtain the secondary breaking state in which the plug main body breaking ring portion 50 separates the plug main body breaking portion 31a from the plug main body 31.

Thus, the plug main body breaking ring portion having the finger-put-on ring is provided in the plug main body breaking portion constituting the plug main body, and thereby the plug main body breaking portion which is a part of the plug main body can easily be broken by putting the finger on the finger-put-on ring to apply the tensile load. In this case, as with the first embodiment, the plug frame whose plug main body breaking portion is separated maintains the state in which the plug frame is continued in the circumferential direction thereof, so that the cylindrical shape which is detachably attached to the venting cap of the channel opening can be maintained and the plug frame can be prevented from unintentionally dropping out from the venting cap.

Figure 20:
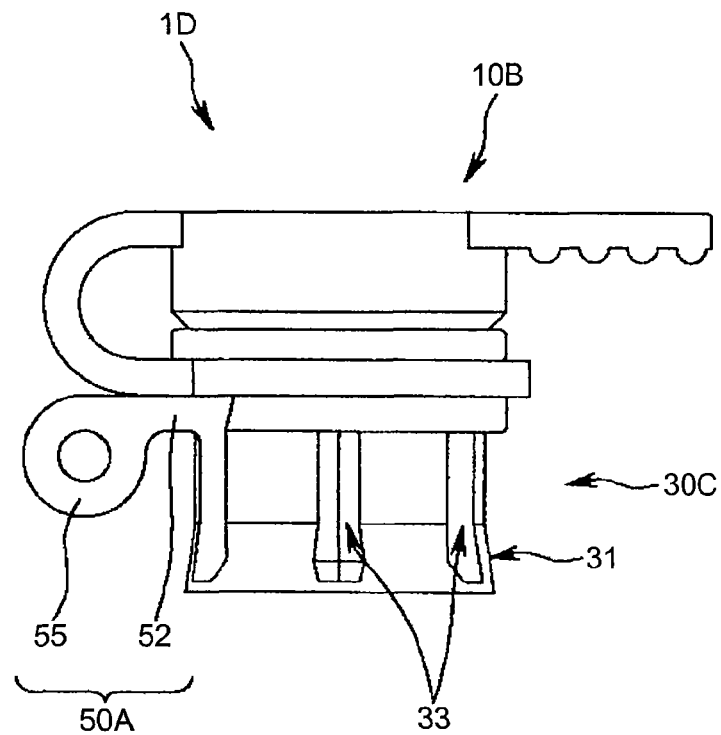
FIG. 20 is a view explaining a variant of the endoscope plug body according to the second embodiment of the invention.
Figure 21:
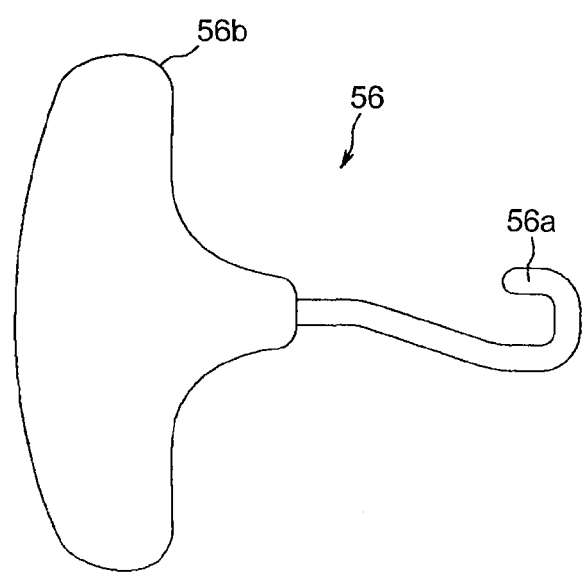
FIG. 21 is a view showing an example of a breaking tool used for the endoscope plug body according to the second embodiment of the invention.

As shown in FIG. 20 which explains a variant of the endoscope plug body, in place of the ring portion 51, a jig arranging ring 55 may be provided in the coupling portion 52 to form an endoscope plug body 1D having a plug main body breaking ring portion 50A. Therefore, as shown in FIG. 21 which shows a breaking jig, a bent portion 56a of a breaking jig 56 having a grip portion 56b is arranged in the jig arranging ring 55, and the grip portion 56b is grasped to apply the load F3 to the plug main body breaking ring portion 50A. Accordingly, the same effect as the second embodiment is obtained in the variant, and the plug main body breaking portion which is a part of the plug main body can more easily be broken.

Figure 22:
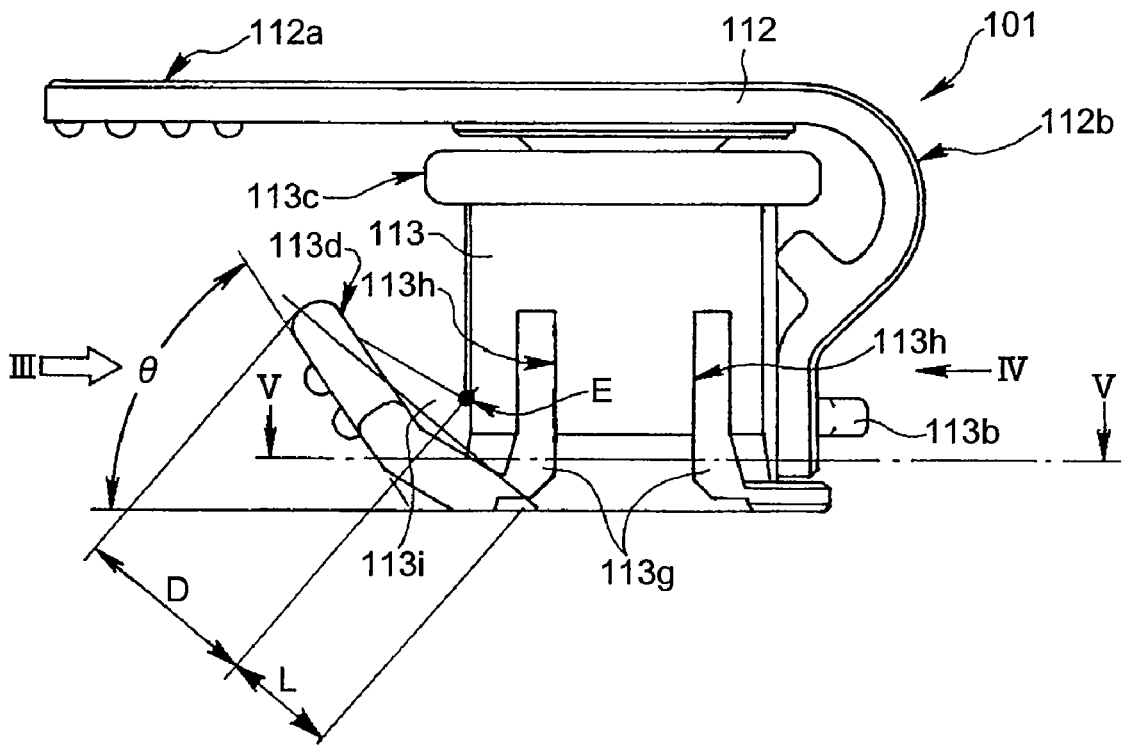
FIG. 22 is a side view schematically illustrating an endoscope plug body according to a third embodiment of the invention.
Figure 23:
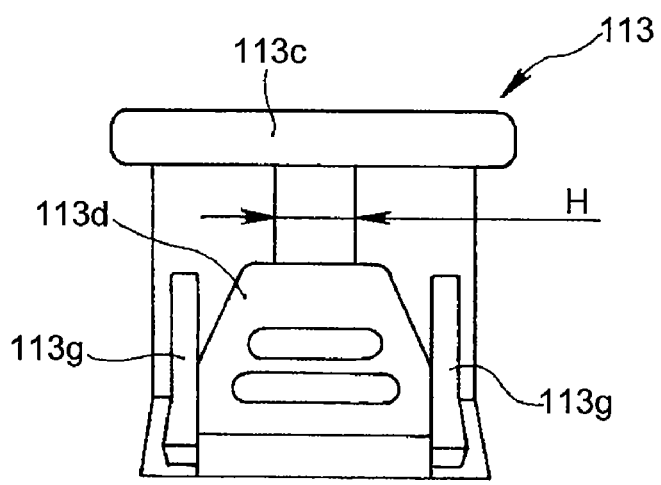
FIG. 23 is a view showing only a plug frame in the endoscope plug body according to the third embodiment of the invention when viewed from a direction indicated by the numeral III of FIG. 22.
Figure 24:
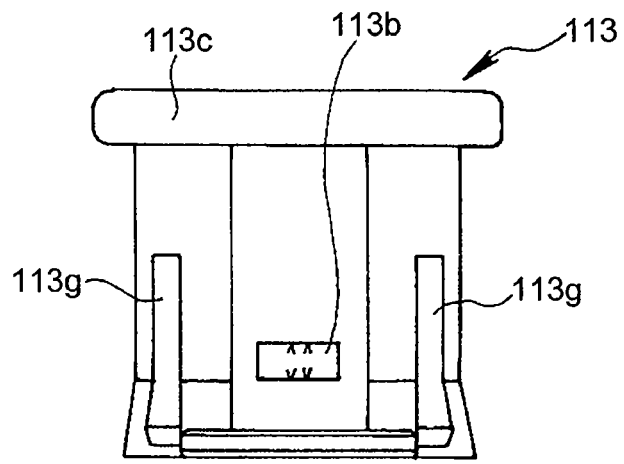
FIG. 24 is a view showing only the plug frame in the endoscope plug body according to the third embodiment of the invention when viewed from the direction indicated by the numeral IV of FIG. 22.
Figure 25:
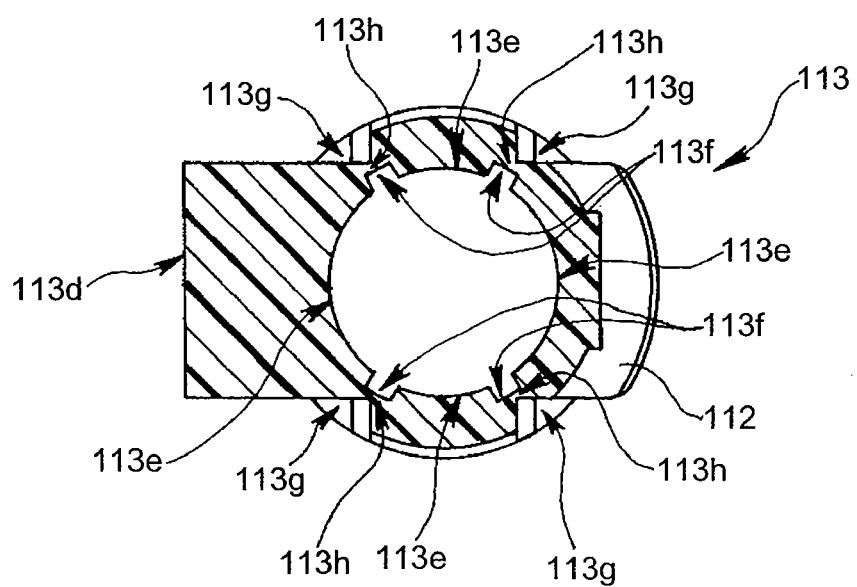
FIG. 25 is a sectional view taken along line V-V of FIG. 22 for showing a cross section of the plug frame in the endoscope plug body according to the third embodiment of the invention.
Figure 26:
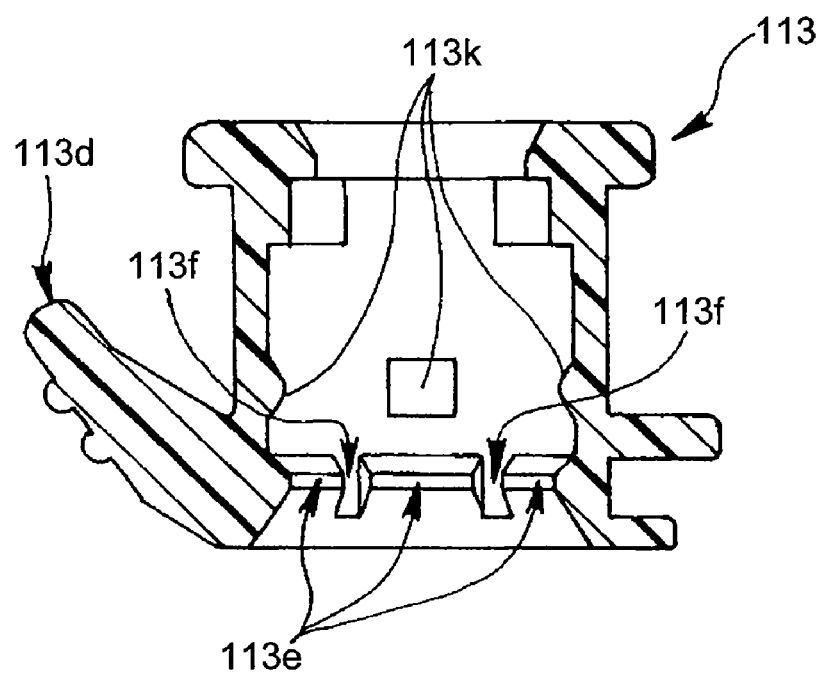
FIG. 26 is a sectional side view of the plug frame in the endoscope plug body according to the third embodiment of the invention.
Figure 27:
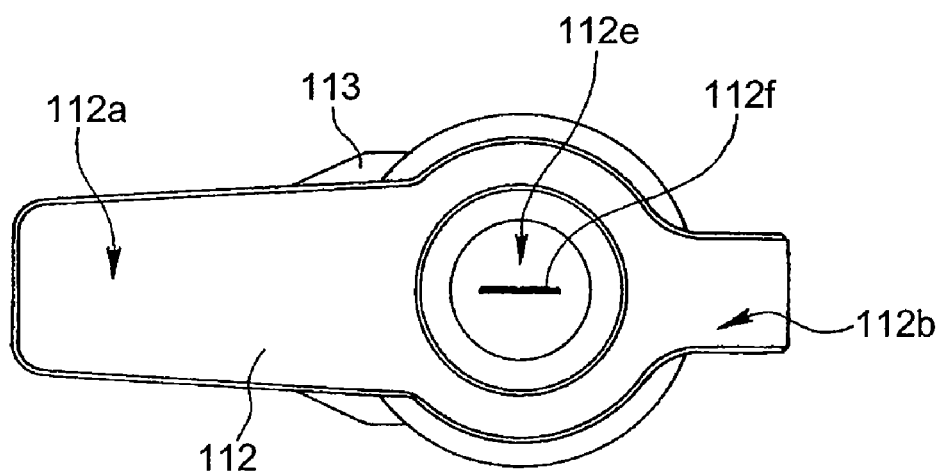
FIG. 27 is a top view showing the endoscope plug body of FIG. 22.
Figure 28:
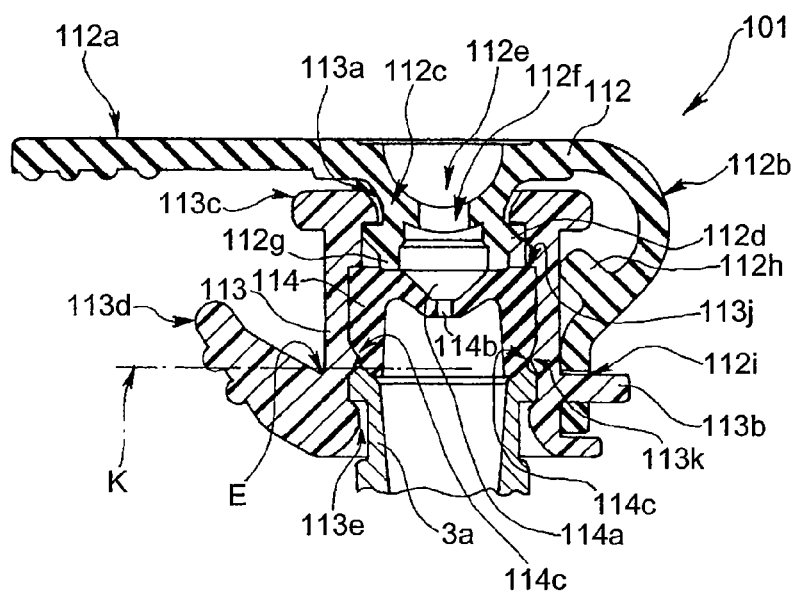
FIG. 28 is a sectional side view showing a state in which the endoscope plug body according to the third embodiment of the invention is attached to a venting cap of a channel opening.

A detailed endoscope plug body according to a third embodiment of the invention will be described below. FIG. 22 is a side view of an endoscope plug body of the third embodiment. FIG. 23 is a view showing only a plug frame in the endoscope plug body when viewed from a direction indicated by the numeral III of FIG. 22. FIG. 24 is a view showing only the plug frame when viewed from the direction indicated by the numeral IV of FIG. 22. FIG. 25 is a sectional view taken along line V-V of FIG. 22 for showing a cross section of the plug frame. FIG. 26 is a sectional side view of the plug frame. FIG. 27 is a top view showing the endoscope plug body of the third embodiment when viewed from above. FIG. 28 is a sectional side view showing a state in which the endoscope plug body is attached to a venting cap of a channel opening.

An endoscope plug body 101 of the third embodiment is attached to the channel opening 3 in place of the endoscope plug body 1 of the first embodiment. Specifically, the endoscope plug body 101 mainly includes a cap member 112, a plug frame 113, and a plug member 114. The cap member 112 is formed by an elastic member such as silicone rubber, butyl rubber, and natural rubber. The plug frame 113 is formed by a resin member such as polyethylene and polypropylene, and the plug frame 113 is mounted on the venting cap 3a of the channel opening 3. The plug member 114 is formed by an elastic member such as silicone rubber, butyl rubber, and natural rubber, and the plug member 114 is retained in the plug frame 113.

The plug member 114 has the substantially same structure as the plug member 20 of the endoscope plug body 1 of the first embodiment. Specifically, the plug member 114 is formed in the substantially cylindrical shape, and the plug member 114 is retained in the plug frame 113 as described above. In the upper end portion of the plug member 114, an upper-surface outer peripheral edge portion abuts on a latching projection portion 113j formed in the plug frame 113. In the lower end portion of the plug member 114, a latch recess 114c formed on a lower-end outer peripheral surface engages a protrusion 113k formed on the inner peripheral surface of the plug frame 113. Therefore, the plug member 114 is retained in the plug frame 113.

As shown in FIG. 28, a recess 114a whose cross section is formed in the substantial conical shape is formed in the upper surface of the plug member 114. A small hole 114b is made in the central portion of the recess 114a. The small hole 114b has the function substantially similar to that of the round hole 23a made in the plug member 20. For example, various kinds of the treatment instrument 9 are inserted into the small hole 114b. Accordingly, the small hole 114b is formed smaller than sheath outer diameters of various kinds of the treatment instrument 9, so that the small hole 114b is sealed when the treatment instrument 9 is inserted into the small hole 114b.

The lower end portion of the plug member 114 is arranged at the position where the lower end portion faces the venting cap 3a in the state in which the endoscope plug body 101 is attached to the channel opening 3, i.e., in the state in which the plug frame 113 is mounted on the venting cap 3a (see FIG. 28). At this point, the lower end portion of the plug member 114 is arranged while brought into close contact with the inner peripheral edge portion of the venting cap 3a. Accordingly, the lower end portion of the plug member 114 and the inner peripheral edge portion of the venting cap 3a are formed in the shapes in which the watertightness is retained when the both sides are brought into close contact with each other to establish the mounting state.

The cap member 112 has the function substantially similar to that of the cap member 10A of the endoscope plug body 1A which is of the first variant of the first embodiment. Specifically, the cap member 112 has a grip portion 112a and an extension portion 112b. The grip portion 112a functions in the substantially same manner as the tongue portion 12 formed in the cap member 10A, and the grip portion 112a is formed while projected toward one direction in the mode in which the grip portion 112a can be grasped with the finger or the like when the cap member 112 is detached from the plug frame 113. On the other hand, the extension portion 112b corresponds to the coupling portion 13 in the cap member 10A. The extension portion 112b is formed while projected toward the opposite direction to grip portion 112a, and an attachment hole 112i (see FIG. 28) is formed in a terminal portion of the extension portion 112b. An attachment protrusion 113b made on the outer peripheral surface of the plug frame 113 is inserted into the attachment hole 112i. Therefore, the cap member 112 is detachably attached to the plug frame 113.

A fitted portion 112c is molded while being integral with the cap member 112. The fitted portion 112c is an intermediate region between the extension portion 112b and grip portion 112a of the cap member 112. In the fitted portion 112c, the surface facing the upper surface portion of the plug frame 113 is formed so as to be projected toward the side of the plug frame 113 when the cap member 112 is mounted on the plug frame 113. The fitted portion 112c is fitted in a plug frame upper face opening 113a of the plug frame 113. The fitted portion 112c functions as the cap portion which is detachably attached to the plug frame upper face opening 113a of the plug frame 113. A flange portion 112d is formed on the outer peripheral surface close to the front edge of the fitted portion 112c. The maximum outer diameter of the flange portion 112d is formed slightly larger than the inner diameter of the plug frame upper face opening 113a. The fitted portion 112c of the cap member 112 can detachably be attached to the plug frame upper face opening 113a of the plug frame 113 by elastically deforming the fitted portion 112c.

A treatment instrument introducing portion 112e and a slit 112f (also see FIG. 27) are formed in the region where the fitted portion 112c of the cap member 112 is formed. The treatment instrument introducing portion 112e is formed in the shape through which the treatment instrument 9 (see FIG. 1) is easily introduced, and the treatment instrument introducing portion 112e is formed by, e.g., a substantially hemispherical space in cross section. The slit 112f is provided while continued to the treatment instrument introducing portion 112e.

Therefore, even in the state in which the cap member 112 is mounted on the plug frame 113, the treatment instrument 9 (see FIG. 1) can be inserted into the treatment instrument insertion channel 7 from the treatment instrument introducing portion 112e of the cap member 112 through the slit 112f and the small hole 114b of the plug member 114. At this point, the slit 112f and the small hole 114b come into close contact with the outer peripheral surface of the treatment instrument 9, which secures the watertightness between the inside and the outside of the treatment instrument insertion channel 7.

On the other hand, the slit 112f is retained in the substantially closed state to the outside as shown in FIG. 27, when the treatment instrument 9 is not inserted into the treatment instrument insertion channel 7 through the slit 112f and the small hole 114b while the cap member 112 is mounted on the plug frame 113.

As shown in FIG. 28, in the state in which the cap member 112 is mounted on the plug frame 113, the distal end portion 112g of the flange portion 112d is brought into close contact with the upper-surface region of the plug member 114, arranged in the plug frame 113, in the watertight manner.

A convex portion 112h is molded in a predetermined region while being integral with the cap member 112. The convex portion 112h is formed so as to be projected toward the side wall of the plug frame 113. The predetermined region is an intermediate region between the extension portion 112b and attachment hole 112i of the cap member 112, and the predetermined region faces the side wall of the plug frame 113 when the cap member 112 is mounted on the plug frame 113. The region near the distal end portion of the extension portion 112b abuts on the side wall of the plug frame 113, which allows the convex portion 112h to support the extension portion 112b of the cap member 112.

The plug frame 113 is fitted in the venting cap 3a to attach the endoscope plug body 101 to the channel opening 3 while the venting cap 3a is covered with the plug frame 113. Specifically, the plug frame 113 is formed in the substantially cylindrical shape as a whole, and the plug frame upper face opening 113a having the substantially circular shape is made in the upper surface of the plug frame 113. As described above, the flange portion 112d of the fitted portion 112c of the cap member 112 is detachably fitted in the plug frame upper face opening 113a.

The attachment protrusion 113b having the arrow-head shape is provided in the projected manner on the outer peripheral surface of the plug frame 113 while being integral with the outer peripheral surface. As described above, the attachment protrusion 113b is fitted in the attachment hole 112i of the cap member 112, which allows the cap member 112 to be detachably attached to the plug frame 113.

In this case, the maximum width of the arrow-head shape portion close to the front edge of the attachment protrusion 113b is larger than the width of the attachment hole 112i. The width of the base end portion of the attachment protrusion 113b is substantially equal to the width of the attachment hole 112i.

When the attachment protrusion 113b is inserted and fitted into the attachment hole 112i, attachment protrusion 113b passes through the attachment hole 112i while the attachment hole 112i is widened larger than the arrow-head shape portion of the attachment protrusion 113b by the elasticity of the attachment hole 112i, and the attachment hole 112i returns to the original size in the base end portion of the attachment protrusion 113b by restoring force of the attachment hole 112i. Therefore, the fitting state is established between the attachment hole 112i and the attachment protrusion 113b, and the attachment protrusion 113b is not easily disengaged from the attachment hole 112i. Accordingly, the cap member 112 does not easily drop out from the plug frame 113 even if the fitted portion 112c of the cap member 112 is disengaged from the plug frame upper face opening 113a of the plug frame 113.

A plug frame flange portion 113c is formed in the outer edge portion on the upper surface side of the plug frame 113. A protrusion 113d is integrally formed in the outer peripheral surface on the side opposite to the region where the attachment protrusion 113b is formed, and the protrusion 113d is projected toward the outside from the lower end surface of the plug frame 113.

The protrusion 113d corresponds to the protrusion 32 of the endoscope plug body 1 according to the first embodiment. The protrusion 113d functions as a part of the breaking member for breaking the area of the plug frame 113 to detach the endoscope plug body 101 from the channel opening 3 while the continued state is maintained in the circumferential direction of the plug frame 113. Specifically, as shown in FIG. 22, the protrusion 113d is formed toward the obliquely upward direction with an inclined angle θ degrees (°) with respect to the lower end surface of the plug frame 113. In this case, preferably the angle θ degrees (°) are set in the range of 10°<θ<70°.

As shown in FIG. 28, a latch portion 113e which is projected inward is formed in the inner peripheral surface close to the lower end of the plug frame 113. The latch portion 113e functions as an example of the latch member for attaching the plug frame 113 to the venting cap 3a by latching the latch portion 113e along the outer periphery of the venting cap 3a. Specifically, the latch portion 113e has the function of preventing the plug frame 113 of itself from dropping out by latching the latch portion 113e in the outer edge portion of the venting cap 3a when the plug frame 113 is mounted on the venting cap 3a. Accordingly, the inner diameter of the latch portion 113e is slightly smaller than the outer diameter of the venting cap 3a. The latch portion 113e of the plug frame 113 can be mounted on the venting cap 3a by elastically deforming the latch portion 113e.

As shown in FIGS. 25 and 26, in the latch portion 113e, notch portions 113f are formed outward from the inner peripheral surface in the four directions. The notch portion 113f corresponds to the recess 39 in the endoscope plug body 1 of the first embodiment. In the outer peripheral surface close to the lower end of the plug frame 113, outer notch portions 113g are formed in regions where the outer notch portions 113g face the notch portions 113f respectively. The outer notch portion 113g corresponds to the V-shape groove 33 in the endoscope plug body 1 of the first embodiment. Thin portions 113h are formed in the outer peripheral portion close to the lower end of the plug frame 113 by forming the notch portions 113f and the outer notch portions 113g. In the substantially same way as the first thin portion 41 formed in the endoscope plug body 1, the thin portion 113h is formed by reducing the thickness of the plug frame 113, and the thin portion 113h functions as an example of the broken portion which is the area where the rupture strength is weakened compared with other areas of the plug frame 113. Specifically, the thin portion 113h is formed to the side above the latch portion 113e so as to traverse the latched portion of the latch portion 113e which is latched in the venting cap 3a. Two of the four thin portions 113h are formed in both side regions on the base end side of the protrusion 113d.

The protrusion 113d in which the thin portions 113h are formed in both the side regions functions as an example of the operation portion which performs the breaking operation for applying the predetermined load to break the thin portion 113h. The protrusion 113d breaks the thin portions 113h formed in both the side regions, and thereby the protrusion 113d can break the partial area of the plug frame 113 including a part of the latched portion of the latch portion 113e, while the shape is maintained in the continued state in the circumferential direction of the plug frame 113 without breaking the plug frame flange portion 113c.

The broken portion illustrated in the thin portion 113h is the area which is broken in breaking the partial area of the plug frame 113 including a part of the latched portion of the latch portion 113e. Therefore, the broken portion may traverse the latch portion 113e along both the side regions of the protrusion 113*d*, i.e., along the sides of the partial area of the plug frame 113, the broken portion may be formed in the area reaching one end portion (for example, near the end portion of the opening into which the venting cap 3*a* is inserted) of the plug frame 113, and the broken portion may have the rupture strength weaker than those of other areas of the plug frame 113. In this case, the broken portion may be formed by reducing the thickness of the plug frame 113 like the thin portion 113*h*, and the broken portion may be formed in a perforation where through holes are intermittently made to weaken the rupture strength in the area.

In the protrusion 113*d*, as shown in FIG. 22, a rib 113*i* is formed in the surface facing the cylindrical outer peripheral surface of the plug frame 113. The rib 113*i* is formed so as to connect the protrusion 113*d* and the cylindrical outer peripheral surface of the plug frame 113. As shown in FIG. 23, the rib 113*i* is formed while having a width H. The upper end portion (see the letter E of FIGS. 22 and 28) of the rib 113*i* on the side of the plug frame 113 is arranged below the upper end surface (see the letter K of FIG. 28) of the venting cap 3*a*.

In attaching the endoscope plug body 101 to the channel opening 3, i.e., in mounting the plug frame 113 on the venting cap 3*a*, the inner diameter of the latch portion 113*e* is widened up to the outer diameter of the venting cap 3*a* by the elasticity of the plug frame 113, which allows the plug frame 113 to be mounted on the venting cap 3*a*. At this point, each of the thin portions 113*h* is evenly stretched with no breakage.

The action of the endoscope plug body 101 in detaching the endoscope plug body 101 of the third embodiment having the above configuration from the channel opening 3 will be described below.

Figure 29:
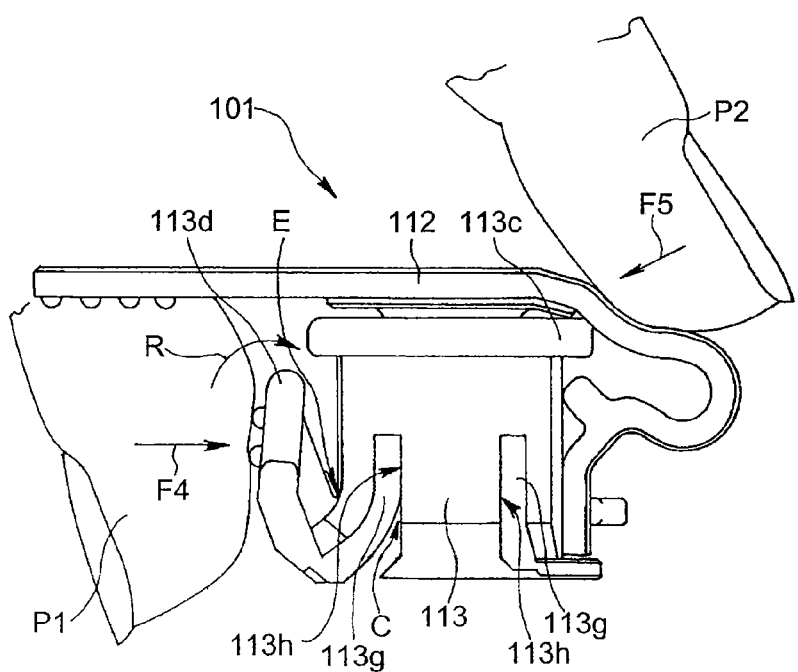
FIG. 29 is a view explaining action of the endoscope plug body according to the third embodiment of the invention.
Figure 30:
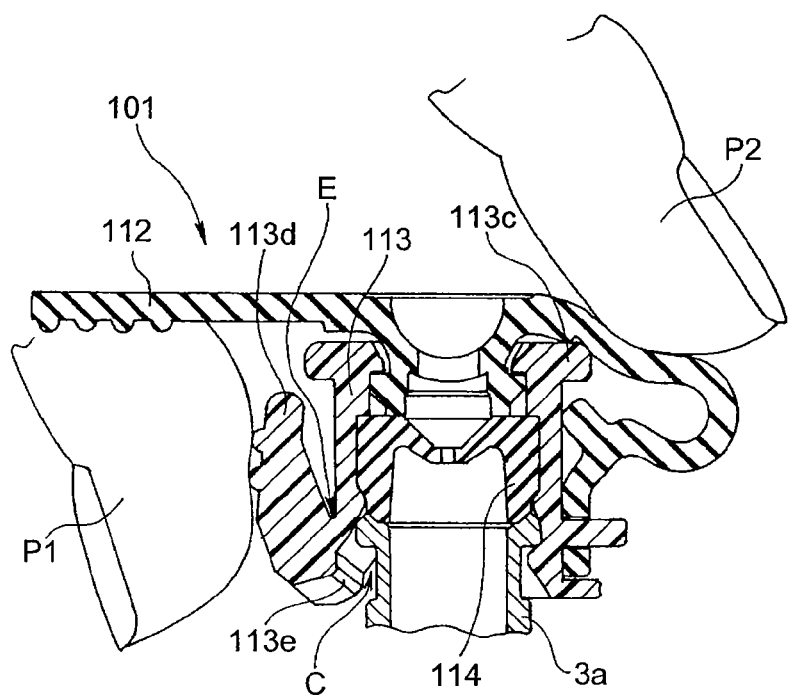
FIG. 30 is a sectional side view showing the endoscope plug body in the state shown in FIG. 29.

FIGS. 29 and 30 are views explaining the action of the endoscope plug body of the third embodiment. FIG. 29 is an appearance view showing the state in which the endoscope plug body of the third embodiment is detached from the channel opening when viewed from a side face of the endoscope plug body, and FIG. 30 is a sectional side view showing the endoscope plug body in the state shown in FIG. 29.

In detaching the endoscope plug body 101 of the third embodiment from the channel opening 3 (namely, the plug frame 113 is detached from the venting cap 3*a*), as shown in FIG. 29, the load is applied in the direction (directions indicated by arrows F4 and F5) in which the endoscope plug body 101 is clamped across the cap member 112 with two fingers P1 and P2. For example, the load is applied to the protrusion 113*d* of the plug frame 113 toward the direction of the arrow F4 with a thumb P1, while the load is applied to the neighbor of the region opposite to the side of the protrusion 113*d* in the plug frame flange portion 113*c* of the plug frame 113 toward the direction of the arrow F5 with a forefinger P2. In this case, because the venting cap 3*a* is made of metal or the like, the venting cap 3*a* is never deformed.

When the load is applied to the protrusion 113*d*, the protrusion 113*d* is rotated in the direction of an arrow R shown in FIG. 29 about an upper end portion E (see FIGS. 22 and 28 to 30) of the rib 113*i* on the side of the plug frame 113. Therefore, the thin portions 113*h* in both the side regions on the base end side of the protrusion 113*d* are broken in time (see the letter C portion of FIG. 29).

In this case, as shown in FIG. 22, assuming that D is a distance from the upper end portion E (rotating fulcrum) of the rib 113*i* on the side of the plug frame 113 to the front edge of the protrusion 113*d* and L is a distance from the upper end portion E of the rib 113*i* on the side of the plug frame 113 to the lower end portion of the thin portion 113*h* of the plug frame 113, the following relationship holds:

$$D > L$$

When a predetermined load is applied to the protrusion 113*d* by a principle of leverage, because the large load is applied to the thin portion 113*h*, the thin portion 113*h* is easily broken. In this case, in the thin portion 113*h*, the breakage proceeds from one end portion (for example, near the end portion of the opening into which the venting cap 3*a* is inserted) of the plug frame 113 toward the direction in which the breakage traverses the latched portion of the latch portion 113*e*, and the breakage of the thin portion 113*h* separates a part of the latched portion of the latch portion 113*e*.

As described above, the thin portion 113*h* is broken, and the lower end portion (i.e., the partial area of the plug frame 113 including a part of the latched portion of the latch portion 113*e*) of the protrusion 113*d* is turned up while the shape is maintained in the continued state in the circumferential direction of the plug frame 113 without breaking the plug frame flange portion 113*c* and the neighbor area of the plug frame flange portion 113*c*. This enables the latched state of the latch portion 113*e* to be released from the venting cap 3*a* as shown in FIG. 30. Therefore, the endoscope plug body 101 can easily be detached from the channel opening 3 (specifically venting cap 3*a*).

In this case, the user retains the endoscope plug body 101 with the two fingers before the breakage is generated at the predetermined point. Accordingly, after the breakage is generated at the predetermined point, the user can detach the endoscope plug body 101 from the channel opening 3 while retaining the endoscope plug body 101 with the two fingers, and the detached endoscope plug body 101 can directly be scrapped.

Thus, according to the third embodiment of the invention, while the endoscope plug body 101 is retained by grabbing the endoscope plug body 101 with the two fingers, the load is applied with the two fingers, and thereby the predetermined region (predetermined region in plural thin portions 113*h*) of the endoscope plug body 101 can extremely easily be broken. Therefore, the partial area of the plug frame 113 including a part of the latched portion of the latch portion 113*e* can be broken while the continued state is maintained in the circumferential direction of the plug frame 113, and the same effect as the first embodiment is obtained. The endoscope plug body 101 can easily be detached from the channel opening 3 and scrapped while kept in the retained state.

The detachment working and scrap working are facilitated in the endoscope plug body 101, and the endoscope plug body 101 is always kept in the retained state, so that a risk of causing the endoscope plug body 101 to mistakenly drop out can be decreased. Accordingly, the body fluid and filth adhering to the endoscope plug body 101 can be prevented from contaminating the floor and the clothes of the worker to always secure a hygienical working environment.

Because the plural thin portions 113*h* are evenly formed, the thin portions 113*h* are evenly elastically deformed when the plug frame 113 of the endoscope plug body 101 is mounted on the venting cap 3*a*. Accordingly, only a part of the plural thin portions 113*h* is never broken, and the stable mounting state can be obtained.

The used endoscope plug body 101 is always in the broken state, the failures such as the wrong use of the used endoscope plug body 101 can securely be suppressed, and the new endoscope plug body 101 can always be provided. Accordingly, the hygienical usage environment can always be secured.

An endoscope plug body according to a fourth embodiment of the invention will be described below.

Figure 31:
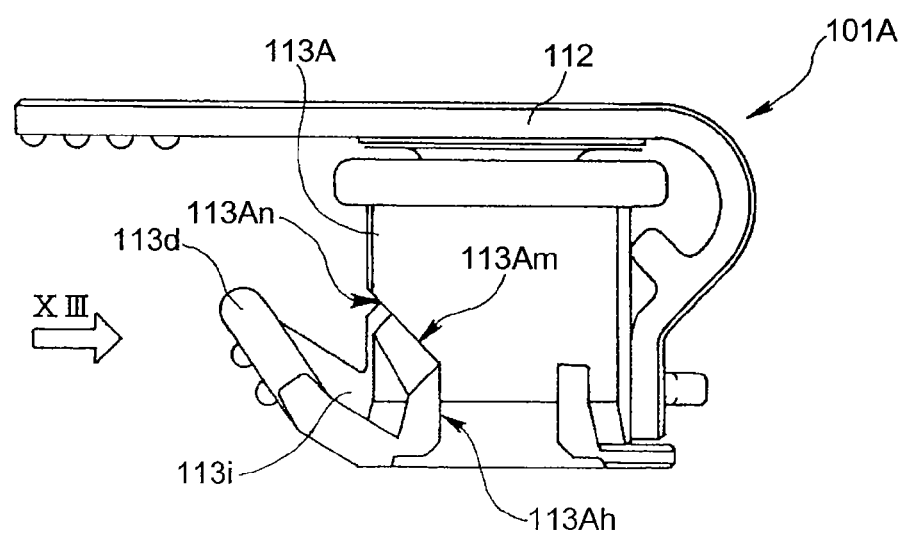
FIG. 31 is a side view schematically illustrating an endoscope plug body according to a fourth embodiment of the invention.
Figure 32:
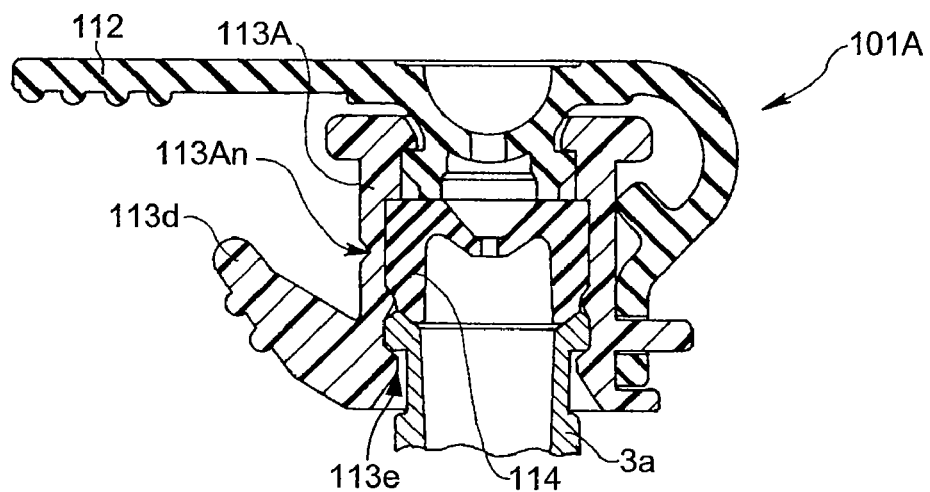
FIG. 32 is a sectional side view in a state in which the endoscope plug body according to the fourth embodiment of the invention is attached to the venting cap of the channel opening.
Figure 33:
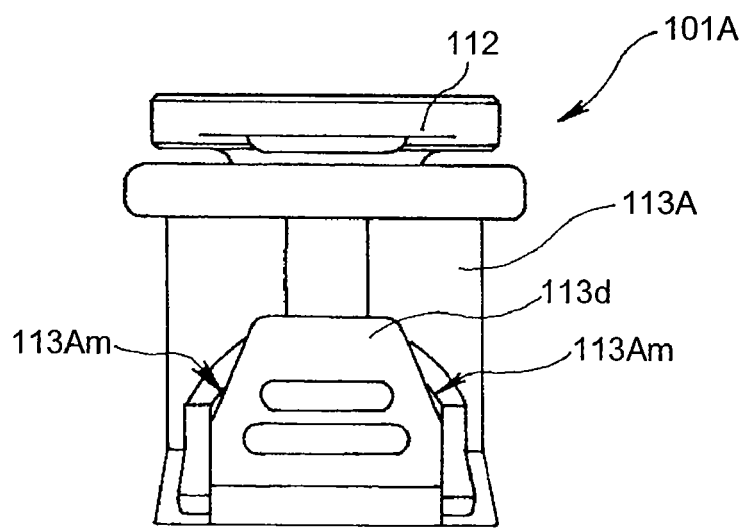
FIG. 33 is a view showing only the plug frame in the endoscope plug body according to the fourth embodiment of the invention when viewed from the direction indicated by the numeral XIII of FIG. 31.

FIG. 31 is a side view showing the endoscope plug body of the fourth embodiment. FIG. 32 is a sectional side view in a state in which the endoscope plug body of FIG. 31 is attached to the venting cap of the channel opening. FIG. 33 is a view showing only the plug frame in the endoscope plug body when viewed from the direction indicated by the numeral XIII of FIG. 31.

The basic configuration of the fourth embodiment is substantially similar to that of the third embodiment. However, the fourth embodiment differs slightly from the third embodiment in the configuration of the thin portion formed in the plug frame. Accordingly, the detailed description will not be repeated for the same configuration as the third embodiment, and only the different configuration will be described below.

In the endoscope plug body 101 of the third embodiment, as shown in FIG. 22 and the like, the thin portion 113h of the plug frame 113 is formed in the lengthwise direction, e.g., vertical direction of the plug frame 113.

On the other hand, in an endoscope plug body 101A of the fourth embodiment, as shown in FIGS. 31 and 32, thin portions 113Ah formed in both the side regions base end side of the protrusion 113d of a plug frame 113A is formed upward from the lower end to a predetermined region (for example, the region which traverses the latched portion of the region latch portion 113e) of the plug frame 113A among the plural thin portion formed in the plug frame 113A. Furthermore, second thin portions 113Am are formed in the endoscope plug body 101A of the fourth embodiment. The second thin portion 113Am is continued to the thin portion 113Ah, the second thin portion 113Am is extended at a predetermined region toward the obliquely upward direction on the side of the protrusion 113d, and the second thin portion 113Am is formed on the outer peripheral side of the plug frame 113A.

A hinge portion 113An is provided in the direction in which the second thin portion 113Am is extended and in the region where the second thin portion 113Am is merged with the outer periphery of the plug frame 113A. The thickness of the hinge portion 113An is larger than the thicknesses of the thin portion 113Ah and second thin portion 113Am, and the thickness of the hinge portion 113An is slightly smaller than the thickness of the outer periphery of the plug frame 113A (also see FIG. 33).

Other configurations are exactly similar to those of the third embodiment.

The action of the endoscope plug body 101A of the fourth embodiment having the above configuration in detaching the endoscope plug body 101A from the channel opening 3 will be described below.

Figure 34:
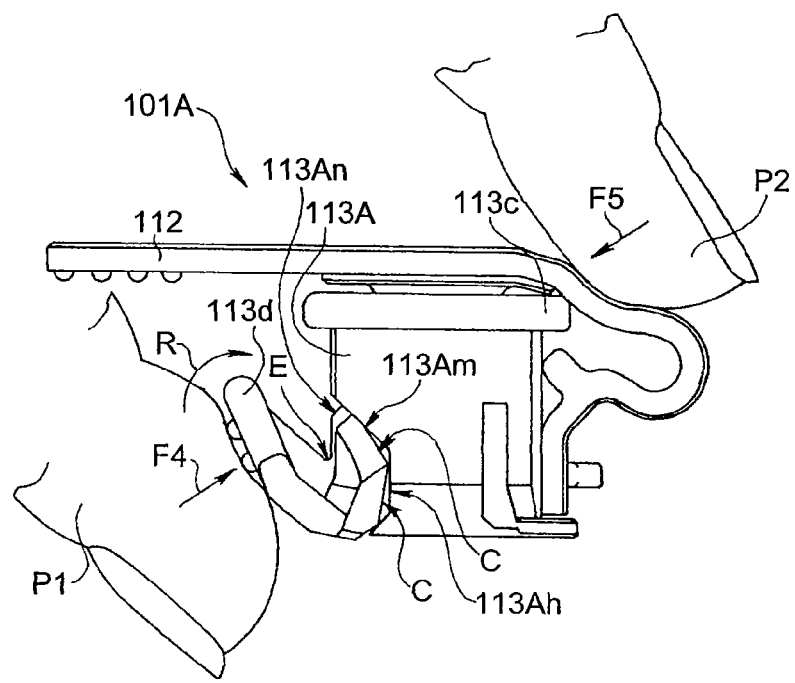
FIG. 34 is a view explaining the action of the endoscope plug body according to the fourth embodiment of the invention.
Figure 35:
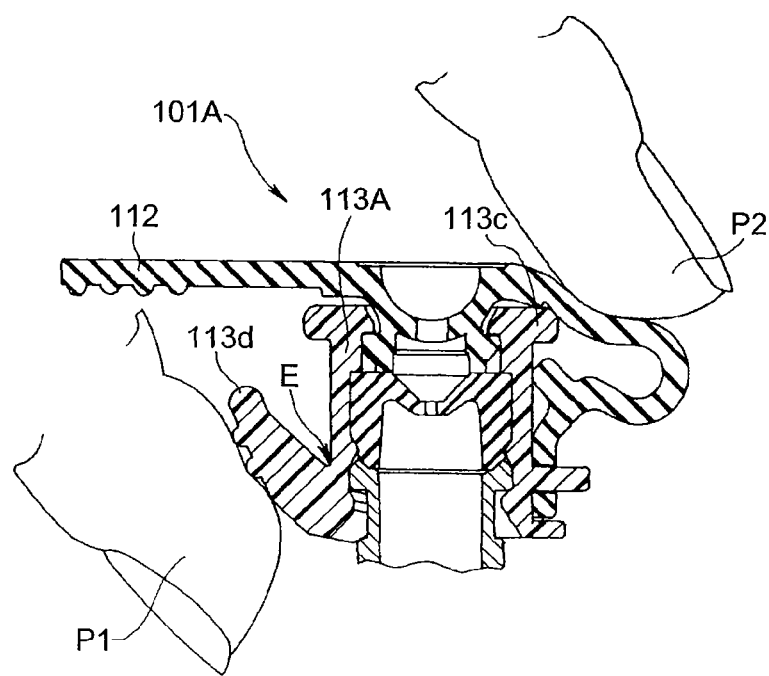
FIG. 35 is a sectional side view showing the endoscope plug body in the state shown in FIG. 34.
Figure 36:
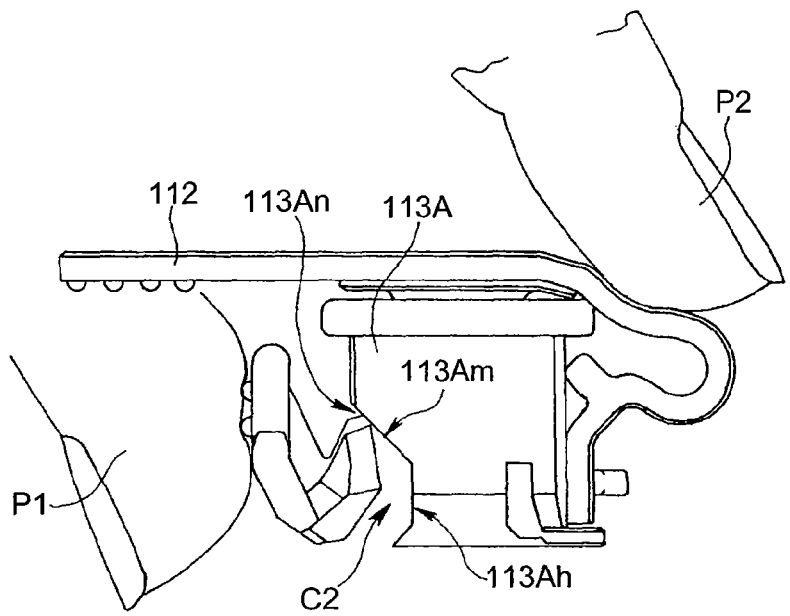
FIG. 36 is a side view showing the endoscope plug body in the state in which an additional load is applied to the endoscope plug body to the state shown in FIGS. 34 and 35.
Figure 37:
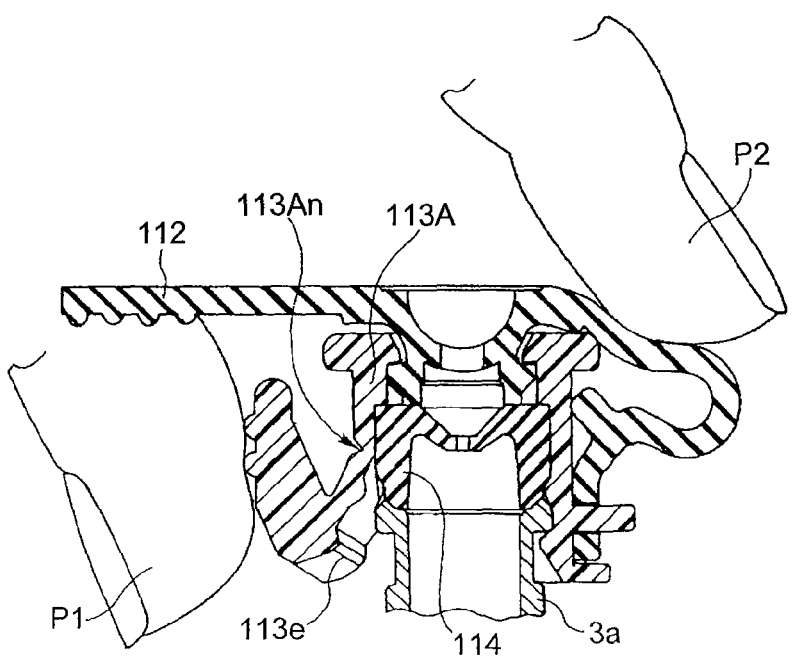
FIG. 37 is a sectional side view showing the endoscope plug body in the state shown in FIG. 36.

FIGS. 34 to 37 are a view explaining the action of the endoscope plug body of the fourth embodiment. FIG. 34 is an appearance view showing a state in which the load applied to the endoscope plug body is started in detaching the endoscope plug body from the channel opening when viewed from the side face of the endoscope plug body. FIG. 35 is a sectional side view showing the endoscope plug body in the state shown in FIG. 34. FIG. 36 is a side view showing the endoscope plug body in which an additional load is applied to the endoscope plug body to the state shown in FIGS. 34 and 35. FIG. 37 is a sectional side view showing the endoscope plug body in the state shown in FIG. 36.

In disengaging the endoscope plug body 101A of the fourth embodiment from the channel opening 3 (namely, the plug frame 113A is detached from the venting cap 3a), as shown in FIGS. 34 and 35 (similarly to the third embodiment), the load is applied in the direction (directions indicated by the arrows F4 and F5) in which the endoscope plug body 101A is clamped across the cap member 112 with the two fingers P1 and P2. For example, the load is applied to the protrusion 113d of the plug frame 113A toward the direction of the arrow F4 with the thumb P1, while the load is applied to the neighbor of the region opposite to the side of the protrusion 113d in the plug frame flange portion 113c of the plug frame 113A toward the direction of the arrow F5 with the forefinger P2. In this state, the protrusion 113d is rotated in the direction of the arrow R shown in FIG. 34 about the upper end portion E of the rib 113i on the side of the plug frame 113A by applying the load to the protrusion 113d. Therefore, a crack C is generated in the thin portion 113Ah and second thin portion 113Am of both the side regions on the base end side of the protrusion 113d.

When the load is further applied to the protrusion 113d in the same direction, the state shown in FIGS. 36 and 37 is obtained. At this point, the crack portion designated by the letter C of FIG. 34 becomes a crack C2 which is further widened.

Accordingly, in the state shown in FIGS. 36 and 37, the crack C2 can be widened with the lesser load. That is, the thin portion 113Ah and the second thin portion 113Am are broken about the hinge portion 113An by applying the load to the protrusion 113d.

As described above, the hinge portion 113An is formed while having the thickness larger than that of the second thin portion 113Am, and the hinge portion 113An becomes the rotating center after the crack C2 is generated, so that the load in the stretching direction is never applied. Accordingly, the breakage is not generated in the hinge portion 113An, and the protrusion 113d is maintained in the state in which the protrusion 113d is connected to the plug frame 113A through the hinge portion 113An.

In the state shown in FIGS. 36 and 37, while the shape is maintained in the continued state in the circumferential direction of the plug frame 113A without breaking the plug frame flange portion 113c and the neighbor area of the plug frame flange portion 113c, the partial area of the plug frame 113A including a part of the latched portion of the latch portion 113e is turned up, and a part of the latch portion 113e is separated from the opening edge portion of the venting cap 3a. Therefore, the engagement can easily be released between the endoscope plug body 101A and the venting cap 3a. Accordingly, the endoscope plug body 101A can easily be detached from the channel opening 3 (specifically venting cap 3a).

As described above, according to the fourth embodiment of the invention, the same effect as the third embodiment can be obtained. At the same time, in addition to the thin portion 113Ah which is extended in the longitudinal direction of the plug frame 113A, the second thin portion 113Am which is extended in the transverse direction is also formed. The breaking operation can smoothly be performed by applying the load.

Once the crack is generated in the predetermined region of the endoscope plug body 101A to start the breakage, the cut amount of breaking area becomes larger compared with the third embodiment, so that the user can comprehend at a glance whether or not the endoscope plug body 101A is already used. Accordingly, the wrong reuse of the used endoscope plug body 101A can be prevented.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope plug body, comprising
a plug frame with which a venting cap is covered, an inner peripheral surface being formed in the venting cap, the inner peripheral surface being communicated with a channel arranged in an endoscope, said plug frame having an endoscope side; and
a plug member which is held by the plug frame to cover an opening of the venting cap, wherein the plug frame includes
a first end portion arranged at the endoscope side of the plug frame;
a second end portion arranged at a side of the plug frame opposite to the first end portion;
a latch member that latches the plug frame along the periphery of the venting cap to attach the plug frame to the venting cap; and
a breaking member that breaks a partial area of the plug frame the partial area reaching the first end portion of the plug frame while including a part of a latched portion of the latch member,
the plug body being configured such that, when a load is applied to the breaking member in a direction extending from the second end portion to the first end portion to break the partial area, an entire circumference of the plug frame outside the partial area remains unbroken and intact and the plug member remains held by the plug frame to cover the opening.

2. The endoscope plug body according to claim 1, wherein the breaking member separates the partial area from the plug frame.

3. The endoscope plug body according to claim 1, wherein the breaking member includes
a broken portion which traverses the latch portion along a side of the partial area, the broken portion being formed in an area proximate to the first end portion the plug frame, rupture strength being weakened compared with the plug frame in the broken portion; and
an operation portion which is projected on an outer peripheral surface of the plug frame and on a surface in the partial area, the operation portion performing a breaking operation for breaking the broken portion.

4. The endoscope plug body according to claim 3, wherein the operation portion is configured to perform the breaking operation when a load is applied in a direction extending from the second end portion of the plug frame to the first end portion.

5. The endoscope plug body according to claim 4, wherein the operation portion is rotated in a direction in which the venting cap is covered with the plug frame.

6. The endoscope plug body according to claim 3, wherein the broken portion is broken from the second portion of the plug frame toward a direction in which the broken portion traverses the latch portion.

7. The endoscope plug body according to claim 3, further including a rib which connects the operation portion and the plug frame,
wherein an upper end region of the rib is formed at a position lower than an upper end face of the venting cap in a state in which the plug frame is attached to the venting cap.

8. The endoscope plug body according to claim 3, wherein the broken portion includes
a first broken portion which traverses the latch portion along a side of the partial area; and
a second broken portion which is continued to the first broken portion, the second broken portion being formed in a direction perpendicular to or in a direction oblique to a direction in which the first broken portion is formed.

9. The endoscope plug body according to claim 1, comprising a cap member which is separated from the plug frame, the cap member having a cap portion which is arranged in an opening provided in the second end portion of the plug frame,
wherein the plug frame includes a fitting portion which detachably attaches the cap member.

10. The endoscope plug body according to claim 9, wherein the cap member is formed by an elastic member, and the cap portion has a first treatment instrument insertion portion into which an endoscope treatment instrument introduced into the channel is inserted.

11. The endoscope plug body according to claim 1, wherein the plug member is separated from the plug frame, formed by an elastic member, and has a second treatment instrument insertion portion into which the endoscope treatment instrument introduced into the channel is inserted,
the plug frame has an internal space in which the plug member is arranged.

* * * * *